United States Patent
Moon et al.

(10) Patent No.: US 10,791,954 B2
(45) Date of Patent: *Oct. 6, 2020

(54) PORTABLE APPARATUS AND METHOD OF CHANGING SCREEN OF CONTENT THEREOF

(71) Applicant: Samsung Electronics Co., Ltd., Suwon-si, Gyeonggi-do (KR)

(72) Inventors: Sun-ho Moon, Suwon-si (KR); Jong-ho Choi, Suwon-si (KR); Se-jin Kwak, Seoul (KR); Sung-soo Kim, Osan-si (KR); Hwa-kyung Kim, Seoul (KR); Jong-youb Ryu, Suwon-si (KR); Sang-hyup Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/728,482

(22) Filed: Dec. 27, 2019

(65) Prior Publication Data

US 2020/0129083 A1    Apr. 30, 2020

Related U.S. Application Data

(63) Continuation of application No. 16/166,834, filed on Oct. 22, 2018, now Pat. No. 10,561,334, which is a
(Continued)

(30) Foreign Application Priority Data

Apr. 30, 2015  (KR) .................. 10-2015-0061725

(51) Int. Cl.
*A61B 5/0482* (2006.01)
*G06F 3/01* (2006.01)
(Continued)

(52) U.S. Cl.
CPC .......... *A61B 5/0482* (2013.01); *A61B 5/0002* (2013.01); *A61B 5/0478* (2013.01);
(Continued)

(58) Field of Classification Search
None
See application file for complete search history.

(56) References Cited

U.S. PATENT DOCUMENTS 6,483,485 B1   11/2002  Huang et al.
9,144,405 B2    9/2015  Kim et al.
(Continued)

FOREIGN PATENT DOCUMENTS

CN    103414908 A    11/2013
JP     3075971 U      3/2001
(Continued)

OTHER PUBLICATIONS

Korean Notice of Allowance dated Nov. 15, 2019, issued in Korean Application No. 10-2017-0061725.
(Continued)

*Primary Examiner* — Jwalant Amin
(74) *Attorney, Agent, or Firm* — Jefferson IP Law, LLP

(57) ABSTRACT

A portable apparatus and a method of changing a content screen of the portable apparatus are provided. The portable apparatus includes changing a displayed content in response to an increase in a visual fatigue and a method of changing a content screen of the portable apparatus. Some of disclosed various embodiments provide a portable apparatus that calculates a visual fatigue by using user electroencephalogram (EEG) information received from a wearable apparatus and changing a displayed content into another content in response to an increase in the calculated visual fatigue, and a method of changing a content screen of the portable apparatus.

18 Claims, 23 Drawing Sheets

Related U.S. Application Data continuation of application No. 15/078,445, filed on Mar. 23, 2016, now Pat. No. 10,130,279.

(51) Int. Cl.

| | | |
|---|---|---|
| *A61B 5/00* | (2006.01) | |
| *G06F 3/0488* | (2013.01) | |
| *A61B 5/0478* | (2006.01) | |
| *G06K 9/00* | (2006.01) | |
| *G16H 40/63* | (2018.01) | |
| *A61B 3/00* | (2006.01) | |
| *A61B 5/048* | (2006.01) | |
| *A61B 3/113* | (2006.01) | |

(52) U.S. Cl.
CPC .......... *A61B 5/6803* (2013.01); *A61B 5/6898* (2013.01); *A61B 5/742* (2013.01); *A61B 5/7475* (2013.01); *G06F 3/013* (2013.01); *G06F 3/015* (2013.01); *G06F 3/04886* (2013.01); *G06K 9/00496* (2013.01); *G06K 9/00597* (2013.01); *G16H 40/63* (2018.01); *A61B 3/00* (2013.01); *A61B 3/113* (2013.01); *A61B 5/048* (2013.01); *G06F 2203/04806* (2013.01)

(56) References Cited

U.S. PATENT DOCUMENTS

| | | | |
|---|---|---|---|
| 9,268,145 | B2 | 2/2016 | Kato et al. |
| 2010/0137748 | A1 | 6/2010 | Sone et al. |
| 2011/0270123 | A1 | 11/2011 | Reiner |
| 2012/0210245 | A1 | 8/2012 | McCoy et al. |
| 2013/0044291 | A1 | 2/2013 | Kato et al. |
| 2013/0057660 | A1 | 3/2013 | Kim et al. |
| 2013/0229711 | A1 | 9/2013 | Kato et al. |
| 2014/0016837 | A1 | 1/2014 | Nechyba et al. |
| 2014/0081117 | A1 | 3/2014 | Kato et al. |
| 2014/0240362 | A1 | 8/2014 | Kurita |
| 2014/0276090 | A1 | 9/2014 | Breed |
| 2014/0333435 | A1 | 11/2014 | Huang et al. |
| 2014/0347265 | A1 | 11/2014 | Aimone et al. |
| 2015/0051887 | A1 | 2/2015 | Lee |
| 2015/0213634 | A1 | 7/2015 | Karmarkar et al. |
| 2016/0293139 | A1 | 10/2016 | Kwon |

FOREIGN PATENT DOCUMENTS

| | | |
|---|---|---|
| JP | 2002-511950 A | 4/2002 |
| JP | 2004-110546 A | 4/2004 |
| JP | 2004-191628 A | 7/2004 |
| JP | 2005-230030 A | 9/2005 |
| JP | 2012-227752 A | 11/2012 |
| JP | 2013-077013 A | 4/2013 |
| JP | 2013-215356 A | 10/2013 |
| JP | 5503081 B2 | 5/2014 |
| JP | 2014-194540 A | 10/2014 |
| JP | 2015-046885 A | 3/2015 |
| KR | 10-2000-0046835 A | 7/2000 |
| KR | 10-2002-0011615 A | 2/2002 |
| KR | 10-0463345 B1 | 5/2005 |
| KR | 10-2009-0001342 A | 1/2009 |
| KR | 10-2009-0044200 A | 5/2009 |
| KR | 10-2013-0025675 A | 3/2013 |
| KR | 10-1267637 B1 | 5/2013 |
| KR | 10-2014-0021208 A | 2/2014 |
| KR | 10-1402739 B1 | 6/2014 |
| KR | 10-2014-0094851 A | 7/2014 |
| KR | 10-2014-0097675 A | 8/2014 |
| KR | 10-1432044 B1 | 8/2014 |
| WO | 98/05024 A1 | 2/1998 |
| WO | 2010/143455 A1 | 12/2010 |

OTHER PUBLICATIONS

Korean Office Action with English translation dated Aug. 27, 2019; Korean Appin. No. 10-2015-0061725.

PORTABLE APPARATUS AND METHOD OF CHANGING SCREEN OF CONTENT THEREOF

CROSS-REFERENCE TO RELATED APPLICATION(S)

This application is a continuation application of prior Application Ser. No. 16/166,834, filed on Oct. 22, 2018, which is a continuation application of prior Application Ser. No. 15/078,445, filed on Mar. 23, 2016, which was based on and claimed priority under 35 U.S.C. § 119(a) of a Korean patent application filed on Apr. 30, 2015 in the Korean Intellectual Property Office and assigned Serial No. 10-2015-0061725, the entire disclosure of which is hereby incorporated by reference.

TECHNICAL FIELD

The present disclosure relates to a portable apparatus and a method of changing a content screen thereof. More particularly, the present disclosure relates to a portable apparatus that changes a displayed content into another content in response to an increase in a visual fatigue of a user, and a method of changing a content screen thereof.

BACKGROUND

Various types of services and functions that are currently provided from a portable apparatus have been gradually expanded. Also, the portable apparatus provides a screen having a high resolution to a user.

As the user uses a screen having high luminance and high resolution for a long time, a visual fatigue of the user may increase. If the visual fatigue of the user is accumulated, a visual display terminal (VDT) syndrome may appear in the user. Also, eyesight of the user may be deteriorated and/or eye disease of the user may occur due to the accumulation of the visual fatigue of the user.

Therefore, there is a need for an apparatus and method of calculating a visual fatigue of a user and addressing an increase in the visual fatigue of the user.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or the disadvantages and to provide at least the advantages described below. Accordingly, an aspect of the present disclosure is to provide a display apparatus and a method of changing a content screen of a portable apparatus that includes displaying content, receiving bio-information of the user from a wearable apparatus, calculating a visual fatigue based on the bio-information of the user, and displaying other content in response to an increase in the visual fatigue.

In accordance with an aspect of the present disclosure, a portable apparatus is provided. The portable apparatus includes a display unit configured to display content, a communicator configured to be connected to a wearable apparatus, and a controller configured calculate a visual fatigue by using bio-information of the user received from the wearable apparatus through the communicator and display other content in response to an increase in the visual fatigue.

In accordance with another aspect of the present disclosure, a wearable apparatus is provided. The wearable apparatus includes a sensor located in a body of the wearable apparatus and include a measurement electrode and a reference electrode contacting a body of a user, a communicator configured to be connected to a portable apparatus, and a controller configured to detect an electroencephalogram (EEG) of the user using the sensor and transmit EEG information of the user corresponding to the EEG to the portable apparatus through the communicator, wherein the body of the wearable apparatus may have one of a circular shape, an elliptical shape, and a polygonal shape.

A portable apparatus for changing a displayed content into another content in response to an increase in a visual fatigue of a user and a method of changing a content screen of the portable apparatus may be provided.

A portable apparatus for changing a displayed content into another content to relax a visual fatigue in response to an increase in the visual fatigue and a method of changing a content screen of the portable apparatus may be provided.

A portable apparatus for changing a displayed content into various types of contents relaxing a visual fatigue in response to an increase in the visual fatigue and a method of changing a content screen of the portable apparatus may be provided.

A portable apparatus for calculating a visual fatigue of a user by using EEG data of the user and a method of changing a content screen of the portable apparatus may be provided.

A portable apparatus for changing a displayed content into another content in response to an increase in a visual fatigue calculated by using EEG information of a user received from a wearable apparatus and a method of changing a content screen of the portable apparatus may be provided.

A portable apparatus for changing a displayed content into another content including an ocular movement guide in response to an increase in a visual fatigue calculated by using EEG information of the user received from a wearable apparatus and detecting whether an ocular movement of the user is performed, by using a camera and a method of changing a content screen of the portable apparatus may be provided.

In accordance with another aspect of the present disclosure, a portable apparatus that may calculate a visual fatigue by using brainwave information received from an external source, and a method of changing a content screen thereof may be provided.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
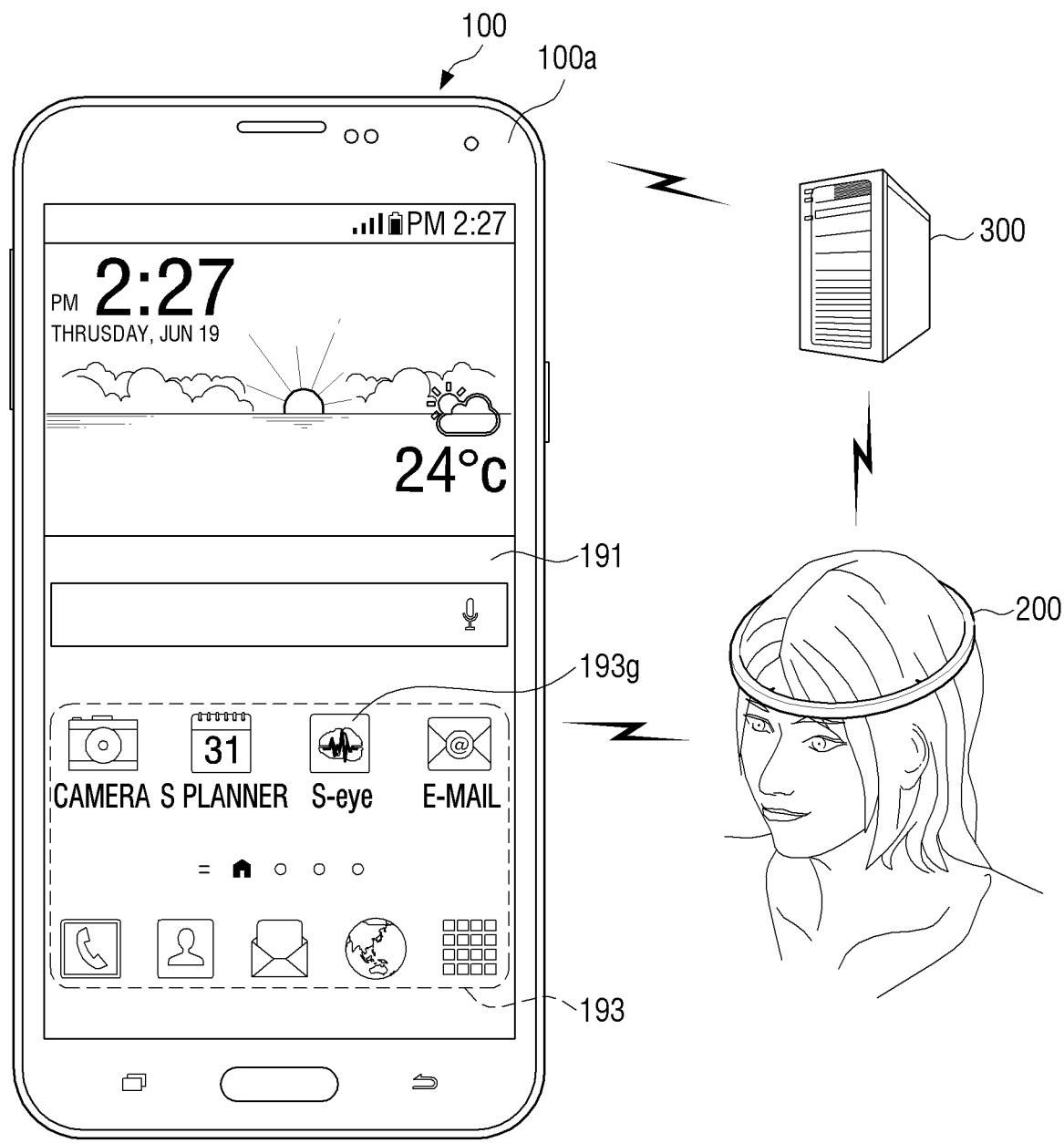
FIG. 1 schematically illustrates a connection between a portable apparatus, a wearable apparatus, and a server according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the following description, the same drawing reference numerals are used for the same elements even in different drawings. The matters defined in the description, such as detailed construction and elements, are provided to assist in a comprehensive understanding of the present disclosure. Thus, it is apparent that the various embodiments of the present disclosure can be carried out without those specifically defined matters. Also, well-known functions or constructions are not described in detail since they would obscure the disclosure with unnecessary detail.

Also, the terms "first", "second", etc. may be used to describe diverse components, but the components are not limited by the terms. The terms are only used to distinguish one component from the others. For example, a first element may be referred to as a second element, and the second element may also be referred to as the first element without departing from the scope of the present disclosure. As used herein, the term "and/or" includes any and all combinations of one or more of the associated listed items.

An application refers to application software that is executed in a computer operating system (OS) or a mobile OS to provide services (or information) to a user. For example, the application may include a word processor, a spread shift, a contacts application, a calendar application, a memo application, an alarm application, a social network system (SNS) application, a chatting application, a map application, a music player, a visual fatigue management application, or a video player. The application according to various embodiments of the present disclosure may refer to a visual fatigue management application that is executed in a portable apparatus or a visual fatigue management application that is executed in a wearable apparatus (e.g., a brainwave measurement wearable apparatus or the like) that is connected to the portable apparatus by wireless or wired. The application according to the various embodiments of the present disclosure may also refer to software that is executed in a portable apparatus in response to a received user input (e.g., a touch or the like).

According to various embodiments of the present disclosure, a status of a wearable apparatus may refer to a context of the wearable apparatus. Status information corresponding to the status of the wearable apparatus may refer to context information of the wearable apparatus. A status change of the wearable apparatus may be the same as a context change of the wearable apparatus.

A widget refers to a mini application that is one of graphic user interfaces (GUIs) that further smoothly support an interaction between a user and an application or an OS. For example, there may be a weather widget, a calculator widget, a watch widget, etc.

A content may be displayed in an application that is executed in a portable apparatus or a wearable apparatus. For example, the content may include a video file or an audio file played in a video player that is one of applications, a music file played in a music player, a photo file displayed in a photo gallery, a webpage file displayed in a web browser, etc. The content may also include a video file, an audio file, a text file, an image file, or a webpage that is displayed or executed in an application. The term "video" used in the various embodiments of the present disclosure may be used as the same meaning as a moving image. Also, the content may include a video file, an audio file, a text file, an image file, or a webpage that is executed in response to a received user input (e.g., a touch or the like).

The content may include an application screen executed in a wearable apparatus and a user interface (UI) configuring the application screen. The content may also include one content or a plurality of contents.

In various embodiments of the present disclosure, a display may include a screen of a touch screen or a screen of a display unit that displays a content.

In various embodiments of the present disclosure, bio-information of a user may include brainwaves, a temperature, pulses, a heartbeat, pulse rate variations, a blood pressure, blood glucose, breath information, oxygen saturation, a skin status, stress, a stress index, sleep information, etc. of a user.

In various embodiments of the present disclosure, a wearable apparatus may refer to a bio-information detecting apparatus that detects bio-information of a user. The bio-information detecting apparatus may be realized as a watch, glasses, a ring, a bracelet, a necklace, a headband, or the like.

In various embodiments of the present disclosure, a change of another content may include a font size of a content displayed in a displayed application, an addition of a color screen to the content, a display of an ocular movement guide in the content, or a display of an ocular movement animation in the content.

A visual fatigue may occur to a user who concentrates on a content displayed in a portable apparatus or views a content for a long time. Surrounding environment elements (e.g., ambient light, temperature, humidity, etc.) causing the visual fatigue and user bio-elements (e.g., corresponding to bio-information such as a body temperature, a heartbeat, etc.) may be diverse. Elements causing the visual fatigue may include dazzle, humidity, bloodshot eyes, dimness of letters, dizziness, lethargy and/or insensibility of eyes, or a physical abnormality degree of eyes. Also, the elements causing the visual fatigue may include a fatigue of a part such as a neck or the like, fatigue of an arm and/or a wrist and/or a shoulder, a fatigue of a leg part, or headache. In addition, elements causing the visual fatigue may include a brightness degree of ambient light or a surrounding noise degree.

In the present application, the terms "include" and "comprise" designate the presence of features, numbers, operations, components, elements, or a combination thereof that are written in the specification, but do not exclude the presence or possibility of addition of one or more other features, numbers, operations, components, elements, or a combination thereof. The like reference numerals in the drawings denote elements that perform the same functions.

FIG. 1 schematically illustrates a connection between a portable apparatus, a wearable apparatus, and a server, according to an embodiment of the present disclosure.

Referring to FIG. 1, the portable apparatus 100, the wearable apparatus 200, and the server 300 may be wirelessly connected to one another by respectively using communicators (refer to FIG. 2) of the portable apparatus 200, the wearable apparatus 200, and the server 300. For example, the portable apparatus 100, the wearable apparatus 200, and the server 300 may be connected to one another in an infra-structure mode where the portable apparatus 100, the wearable apparatus 200, and the server 300 are wirelessly connected to one another through an ad-hoc mode or an access point (AP). The portable apparatus 100 and the wearable apparatus 200 may respectively transmit a content received from the server 300 to each other.

The server 300 may be located around the portable apparatus 100 and the wearable apparatus 200 or may be located remotely from the portable apparatus 100 and the wearable apparatus 200 (e.g., in a cloud server or the like).

For example, a wireless communication may be a wireless local area network (LAN), Wi-Fi, Bluetooth low energy, Zigbee, Wi-Fi direct (WFD), ultra-wideband (UWB), infrared data association (IrDA), near field communication (NFC), or the like but is not limited thereto. Also, the portable apparatus 100, an electronic apparatus, the server 300, and the wearable apparatus 200 may be connected to one another by wire through a connector.

The portable apparatus 100 may receive status change information corresponding to a status change (e.g., turning on and/or off, a brainwave detection, or the like) of the wearable apparatus 200 from the wearable apparatus 200 through an application. The portable apparatus 100 may also receive the status change information corresponding to the status change (e.g., turning on and/or off, the brainwave detection, or the like) of the wearable apparatus 200 through the server 300. The portable apparatus may include a front surface 100a and a back surface (not shown). Also, the portable apparatus 100 may include a home screen 191, which may include an icon menu screen 193 that includes, among others, a shortcut icon 193g.

The portable apparatus 100 may change a status of the wearable apparatus 200 (e.g., may request turning on, a brainwave detection, or the like of the wearable apparatus 200) through one of the application and the server 300.

The portable apparatus 100, the wearable apparatus 200, and the server 300 have been described as being directly connected to one another with reference to FIG. 1. However, the portable apparatus 100, the wearable apparatus 200, and the server 300 may be connected to one another through a sharer, a router, a wireless internet network, or the like.

Figure 2:
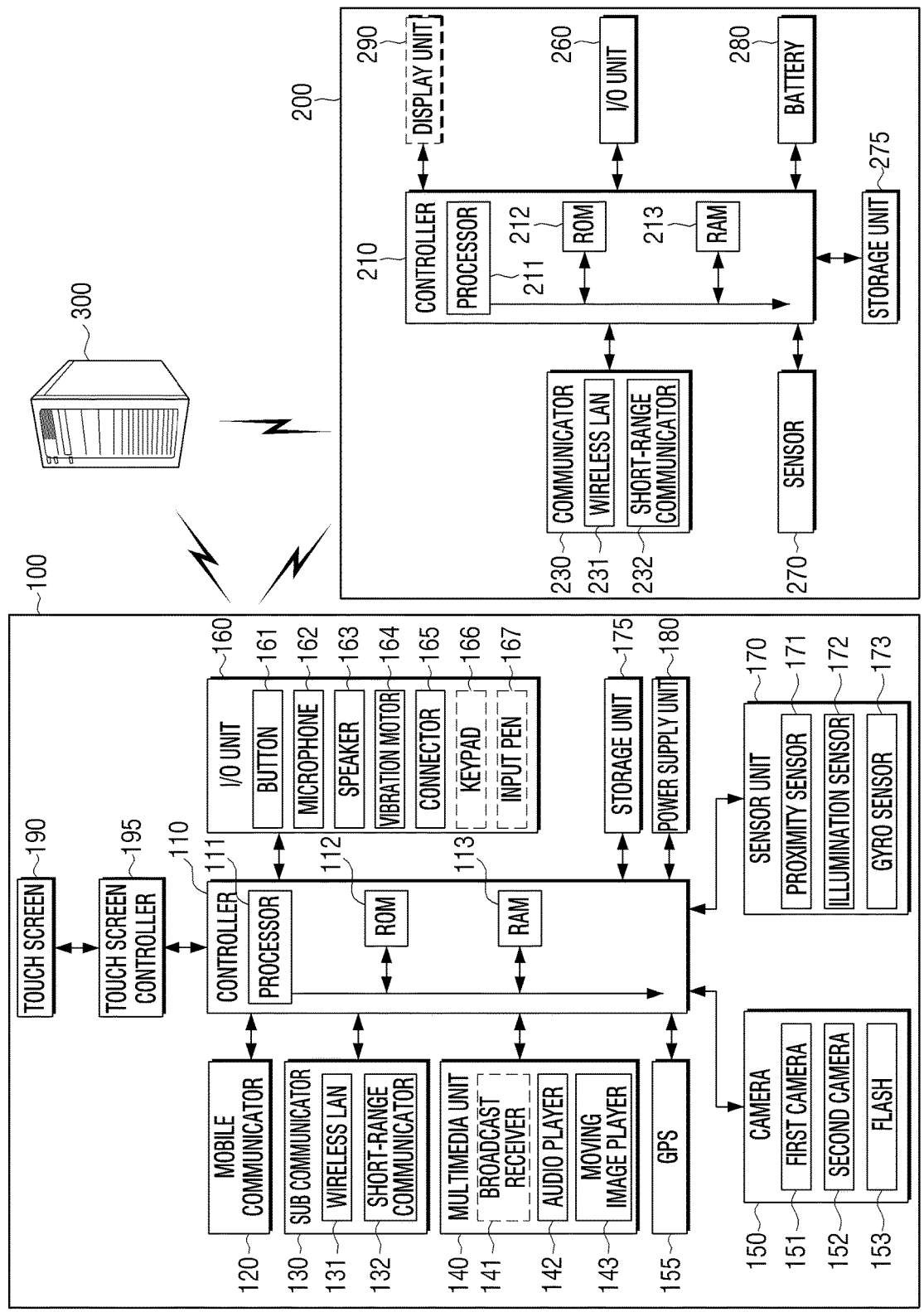
FIG. 2 is a schematic block diagram of a portable apparatus, a wearable apparatus, and a server according to an embodiment of the present disclosure.

FIG. 2 is a schematic block diagram of a portable apparatus, a wearable apparatus, and a server according to an embodiment of the present disclosure.

Referring to FIG. 2, the portable apparatus 100 may be connected to another apparatus (e.g., the wearable apparatus 200 or the server 300) by wire or wirelessly by using a mobile communicator 120, a sub communicator 130, and a connector 165.

The portable apparatus 100 according to an embodiment may refer to an apparatus that may calculate a visual fatigue of a user by using bio-information and an application including user electroencephalogram (EEG) received from the wearable apparatus 200 and/or an apparatus that may infer the visual fatigue of the user by using an application without the bio-information of the user (e.g., EEG) received from the wearable apparatus 200.

The portable apparatus 100 may refer to an apparatus that may change a content displayed on a touch screen or a display unit in response to the calculated visual fatigue. For example, the portable apparatus 100 may include a portable phone, a smartphone, a tablet apparatus, a head-mounted display apparatus having a display unit, a Motion Picture Experts Group (MPEG-1 or MPEG-2) Audio Layer 3 (MP3) player, a moving image player, an electronic bulletin board, a monitor, an electronic apparatus (e.g., a refrigerator, a washer, an air conditioner, or the like) having a display unit, a display apparatus, or the like. The head-mounted display apparatus (not shown) that is one of portable apparatuses 100 may include a sensor (e.g., an electrode) that may detect user EEG. If the visual fatigue detected through the sensor increases, the head-mounted display apparatus including the sensor capable of detecting the user EEG may change a content displayed on a display unit (not shown) into another content capable of reducing the visual fatigue.

It will be easily understood by those skilled in the art that the display apparatus may be realized as an analog television (TV), a digital TV, a 3-dimensional (3D) TV, a smart TV, a light emitting diode (LED) TV, an organic LED (OLED) TV, a plasma TV, a curved TV having a fixed curvature screen, a flexible TV having a fixed curvature screen, a bended TV having a fixed curvature screen, and/or a curvature variable TV capable of changing a curvature of a screen through a user input but is not limited thereto.

The portable apparatus 100 may include a touch screen 190 to transmit data (or a content) to an external source through the mobile communicator 120 or the sub communicator 130 or receive the data (or the content) from the external source through the mobile communicator 120 or the sub communicator 130. The portable apparatus 100 may include an input pen 167 and the touch screen 190 to transmit the data (or the content) to the external source through the mobile communicator 120 or the sub communicator 130 or receive the data (or the content) from the external source through the mobile communicator 120 or the sub communicator 130. The portable apparatus 100 may transmit the data to the external source or receive the data from the external source in response to an interaction (e.g., a touch or a touch gesture) input on the touch screen 190. The portable apparatus 100 may also include a display unit (not shown) having only a display panel (e.g., having no touch panel) to transmit the data (or the content) to the external source or receive the data (or the content) from the external source through the mobile communicator 120 or the sub communicator 130.

The portable apparatus 100 may include a controller 110, the mobile communicator 120, the sub communicator 130, a multimedia unit 140, a camera 150, a global positioning system (GPS) 155, an input/output (I/O) unit 160, a sensor unit 170, a storage unit 175, and a power supply unit 180. The portable apparatus 100 also includes the touch screen 190 and a touch screen controller 195.

The controller 110 may include a processor 111, a read only memory (ROM) 112 that stores a control program for controlling the portable apparatus 100, and a random access memory (RAM) 113 that stores a signal or data input from an outside of the portable apparatus 100 or that is used as a storage area for various types of jobs performed in the portable apparatus 100.

The controller 110 controls an overall operation of the portable apparatus 100 and a signal flow between internal elements 120 through 195 of the portable apparatus 100 and performs a function of processing the data. The controller 110 controls power supplied to the internal elements 120 through 195 by using the power supply unit 180. If an input of the user is received or a set condition is satisfied, the controller 110 may operate a sensor of the sensor unit 170 or may execute an OS or an application stored in the storage unit 175.

The processor 111 may include a graphic processing unit (GPU) (not shown) for graphic processing. The processor 111 may be realized as a system on chip (SoC) including a core (not shown) and a GPU (not shown). The processor 111 may include a single core, a dual core, a triple core, a quad core, and a multiple core. Also, the processor 111, the ROM 112, and the RAM 113 may be connected to one another through a bus.

The controller 110 may control the mobile communicator 120, the sub communicator 130, the multimedia unit 140, the camera 150, the GPS 155, the I/O unit 160, the sensor unit 170, the storage unit 175, the power supply unit 180, the touch screen 190, and the touch screen controller 195.

The controller 110 according to an embodiment displays the content on a screen, is connected to the wearable apparatus 200 through a communicator, calculates a visual fatigue by using EEG information of the user received from the wearable apparatus 200 through the communicator, and changes the content into another content in response to an increase in the visual fatigue.

The controller 110 may display a content, receive EEG information of the user from the wearable apparatus 200, calculate a visual fatigue based on the EEG information of the user, and change the content into another content in response to an increase in the visual fatigue.

The controller 110 may control to request the wearable apparatus 200 to detect EEG through the communicator.

If the other content is a content including an ocular movement guide, the controller 110 may control the other content including the ocular movement guide to execute the camera 150 in response to an execution according to an increase in the visual fatigue.

The controller 110 may control to display different color screens in response to a second application displaying the content.

The controller 110 may control to change the other content in response to the second application displaying the content.

The controller 110 may control to display a pop-up window corresponding to the increase in the visual fatigue.

The controller 110 may control to provide a feedback corresponding to the increase in the visual fatigue.

The term "controller" used herein includes the processor 111, the ROM 112, and the RAM 113.

The mobile communicator 120 may be connected to another apparatus (e.g., the wearable apparatus 200 or the server 300) through a mobile communication network by using one antenna or two or more antennas under control of the controller 110. The mobile communicator 120 may receive EEG data from the wearable apparatus 200 under control of the controller 110. The received EEG data (e.g., analog data or digital data) may be stored in the storage unit 175 under control of the controller 110.

The mobile communicator 120 may transmit and/or receive a wireless signal for a voice call, video call, a text message (e.g., a short message service (SMS)), a multimedia message (e.g., a multimedia messaging service (MMS)), and data communication with a portable phone (not shown), a smartphone (not shown), a tablet personal computer (PC), or another portable apparatus (not shown) having a connectable phone number.

The sub communicator 130 may be connected to another apparatus (e.g., the wearable apparatus 200 or the server 300) through a wireless LAN 131 and a short-range communicator 132 under control of the controller 110. The sub communicator 130 may include at least one selected from the wireless LAN 131 and the short-range communicator 132 (e.g., one or both of the wireless LAN 131 and the short-range communicator 132).

The sub communicator 130 may receive the EEG data from the wearable apparatus 200 under control of the controller 110. The received EEG data (e.g., analog data or digital data) may be stored in the storage unit 175 under control of the controller 110.

The wireless LAN 131 may be wirelessly connected to an AP in a place, where the AP is installed, under control of the controller 110. The wireless LAN 131 may, for example, include Wi-Fi. The wireless LAN 131 supports wireless LAN standard IEEE 802.11x of IEEE. The short-range communicator 132 may perform a short-range communication between the portable apparatus 100 and an external apparatus by wireless without the AP under control of the controller 110. The short-range communication may include Bluetooth, Bluetooth low energy, IrDA, UWB, NFC, etc.

The portable apparatus 100 may include at least one selected from the mobile communicator 120, the wireless LAN 131, and the short-range communicator 132 according to a performance thereof. For example, the portable apparatus 100 may include one of the mobile communicator 120, the wireless LAN 131, and the short-range communicator 132 or a combination of the mobile communicator 120, the wireless LAN 131, and the short-range communicator 132. The portable apparatus 100 may be connected to various types of external accessories (e.g., a wireless speaker, a wireless headset, etc.) by using one of the mobile communicator 120 and the sub communicator 130.

The term "communicator" used herein includes the mobile communicator 120 and the sub communicator 130.

The multimedia unit 140 may receive an external broadcast and play audio and/or a moving image under control of the controller 110. The multimedia unit 140 may include a broadcast receiver 141, an audio player 142, and a moving image player 143.

The broadcast receiver 141 may receive a broadcast signal and additional broadcast information (e.g., an electronic program guide (EPG) or an electronic service guide (ESG)) from an external broadcasting station through an antenna (not shown) under control of the controller 110. Also, the controller 110 may control to play the received broadcast signal and additional broadcast information by using a touch screen, a video codec (not shown), and an audio codec (not shown).

The audio player 142 may play an audio source (e.g., an audio file including file extension mp3, ogg, or way) pre-stored in the storage unit 175 of the portable apparatus 100 or received from an external source by using the audio codec under control of the controller 110.

According to an embodiment of the present disclosure, the audio player 142 may play an auditory feedback corresponding to a content changed in response to an increase in a visual fatigue. For example, the audio player 142 may receive EEG information from the wearable apparatus 200 and analyze the received EEG information to play an auditory feedback (e.g., an output of an audio source stored in a storage unit or the like) corresponding to a content changed in response to an increase in a visual fatigue through an audio codec under control of the controller 110.

According to an embodiment of the present disclosure, the audio player 142 may play an auditory feedback (e.g., an output of an audio source stored in a storage unit or the like) corresponding to a touch detected on the touch screen 190 or consecutive motions of the touch through an audio codec under control of the controller 110.

The moving image player 143 may play a digital moving image source (e.g., a video file including file extension mpeg, mpg, mp4, avi, mov, or mkv), which is pre-stored in the storage unit 175 of the portable apparatus 100 or received from an external source, by using a video codec under control of the controller 110. A multimedia application that may be installed in the portable apparatus 100 may play an audio source or a moving image source by using an audio codec and/or a video codec. The multimedia application that may be installed in the portable apparatus 100 may also play a moving source image by using a hardware codec (not shown) and/or a software codec (not shown).

According to an embodiment of the present disclosure, the moving image player 143 may play a visual feedback corresponding to a content changed in response to an increase in a visual fatigue. For example, the moving image player 143 may receive EEG information from the wearable apparatus 200 and analyze the received EEG information to play a visual feedback (e.g., an output of a moving image source stored in a storage unit or the like) corresponding to a content changed in response to an increase in a visual fatigue through a video codec under control of the controller 110.

It will be easily understood by those skilled in the art that various types of video codecs and audio codecs capable of playing audio and/or video files having various types of file extensions have been produced and sold.

The multimedia unit 140 may include the audio player 142 and the moving image player 143 except the broadcast receiver 141 in response to a performance or a structure of the portable apparatus 100. Also, the controller 110 may be realized to include the audio player 142 or the moving image player 143 of the multimedia unit 140.

The term "audio codec" used herein may include one audio codec or two or more audio codecs. The term "video codec" used herein may include one video codec or two or more video codecs.

The camera 150 may capture a still image or a moving image under control of the controller 110. The camera 150 may include at least one selected from a first camera 151 provided in a front surface (e.g., 100a of FIG. 1) of the portable apparatus 100 and a second camera 152 provided in a back surface (not shown) of the portable apparatus 100. For example, the camera 150 may include one or both of the first camera 151 and the second camera 152. Also, the first camera 151 or the second camera 152 may include a sub light source (e.g., a flash 153) that provides an amount of light necessary for capturing.

The camera 150 may be realized to further include the first camera 151 provided in the front surface and an additional camera (e.g., a third camera (not shown)) adjacent to the first camera 151. For example, a distance between the third camera and the first camera 151 may be realized to be longer than 30 mm and shorter than 80 mm. If the camera 150 further includes the third camera, the controller 110 may capture a 3D still image or a 3D moving image by using the first camera 151 and the third camera.

The camera 150 may be realized to further include the second camera 152 provided in the back surface and an additional camera (e.g., a fourth camera (not shown)) adjacent to the second camera 152. For example, a distance between the fourth camera and the second camera 152 may be realized to be longer than 30 mm and shorter than 80 mm. If the camera 150 further includes the fourth camera, the controller 110 may capture a 3D still image or a 3D moving image by using the second camera 152 and the fourth camera. Also, the cameras 151 and 152 may perform wide-angle capturing, telephoto capturing, and close-up capturing by using an additional lens (not shown) that is removable from an additional adaptor (not shown).

The GPS 155 periodically receives signals (e.g., orbit information, time information, navigation messages, etc. of GPS satellites) from a plurality of GPS satellites that exist on earth's orbit. In an outdoor place, the portable apparatus 100 may calculate locations of the plurality of GPS satellites and a location of the portable apparatus 100 by using signals received from the plurality of GPS satellites and calculate distances between the plurality of GPS satellites and the portable apparatus 100 by using transmission and/or reception time differences. A location, a time, or a movement speed of the portable apparatus 100 may be calculated through a triangulation. An additional GPS satellite may be required for an orbit correction or a time correction. Even indoors, where signals are received from the plurality of GPS satellites through the GPS 155, the portable apparatus 100 may calculate a location, a time, or a movement speed of the portable apparatus 100.

In the outdoor place, the portable apparatus 100 may detect a location or a movement speed by using a wireless AP (not shown). The detection of the location of the portable apparatus 100 may be performed by using a cell-identification (ID) method using an ID of the wireless AP, an enhanced cell-ID method using the ID and a received signal strength (RSS) of the wireless AP, or an angle of arrival (AoA) method using an angle of a signal transmitted from an AP to the portable apparatus 100.

The portable apparatus 100 may also detect the location or the movement speed of the portable apparatus 100 located indoors by using a wireless beacon (not shown). It will be easily understood by those skilled in the art that an indoor location of the portable apparatus 100 may be detected through various types of methods including the above-described method.

The I/O unit 160 may include at least one selected from one button 161 or two or more buttons 161, a microphone 162, a speaker 163, a vibration motor 164, the connector 165, a keypad 166, and the input pen 167.

Figure 5A:
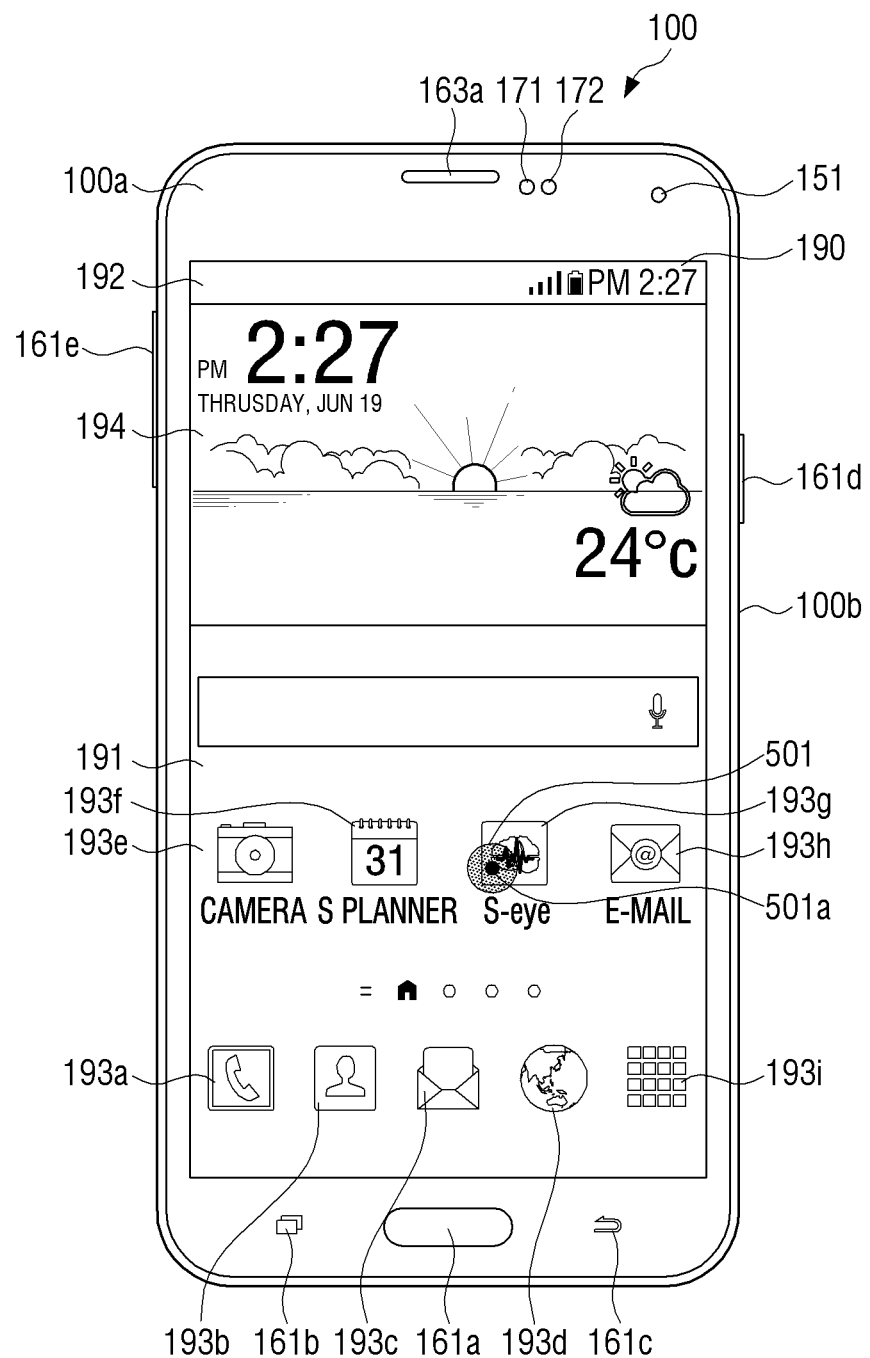
FIGS. 5A to 5F, 6A to 6D, 7A to 7C, 8A and 8B, 9A to 9C, 10A and 10B, and 11A and 11B illustrate a content screen of a portable apparatus according to various embodiments of the present disclosure.

Referring to FIGS. 1 and 5A, the button 161 includes a home button 161a, a menu button 161b, and/or a back button 161c provided in a lower part of the front surface 100a of the portable apparatus 100. The button 161 may include a power and/or lock button 161d and at least one volume button 161e provided in sides thereof. The button 161 of the portable apparatus 100 may also include only the home button 161a, the power and/or lock button 161d, and the volume button 161e. The button 161 of the portable apparatus 100 may be realized as a physical button or a touch button of the touch screen 190. Also, the button 161 of the portable apparatus 100 may be displayed in a text, image, or icon form on the touch screen 190. It will be easily understood by those skilled in the art that a shape, a location, a function, a name, etc. of the button 161 of FIGS. 1 and 5A is only an embodiment for descriptions and thus may be changed, modified, or revised without being limited thereto.

The microphone 162 receives a voice or a sound from an external source to generate an electrical signal under control of the controller 110. The electrical signal generated by the microphone 162 may be converted through an audio codec and then stored in the storage unit 175 or output through the speaker 163 under control of the controller 110. Referring to FIG. 5A, one microphone 162 or two or more microphones 162 may be located in the front surface 100a, a side 100b, and/or the back surface of the portable apparatus 100. One microphone 162 or two or more microphones 162 may be located only in the side 100b of the portable apparatus 100.

The speaker 163 may output sounds corresponding to various types of signals (e.g., a wireless signal, a broadcast signal, an audio source, a moving image file, photo capturing, or the like) decoded by an audio codec under control of the controller 110.

The speaker 163 may output a sound (e.g., a touch manipulation sound corresponding to a phone number input or a photo capturing button manipulation sound) corresponding to a function performed by the portable apparatus 100. Referring to FIGS. 1 and 5A, one speaker 163 or a plurality of speakers 163 may be located in the front surface 100a, the side 100b, and/or the back surface of the portable apparatus 100. One speaker 163 or a plurality of speakers 163 may be located in the front surface 100a of the portable apparatus 100. One speaker 163 may be located in each of the front surface 100a and the back surface of the portable apparatus 100. One speaker 163a may be located in the front surface 100a of the portable apparatus 100, and a plurality of speakers (not shown) may be located in the back surface of the portable apparatus 100.

A plurality of speakers (not shown) may be located in the side 100b of the portable apparatus 100. The portable apparatus 100 where an additional speaker (not shown) is located in the side 100b may provide a user with a sound effect distinguished from another portable apparatus (not shown) where speakers are located in a front surface and a back surface.

According to an embodiment of the present disclosure, the speaker 163 may output an auditory feedback corresponding to a content changed in response to an increase in a visual fatigue. For example, the speaker 163 may receive EEG information from the wearable apparatus 200 and analyze the received EEG information to output an auditory feedback corresponding to a content changed in response to an increase in a visual fatigue under control of the controller 110.

The vibration motor 164 may convert an electrical signal into a mechanical vibration under control of the controller 110. The vibration motor 164 may include a linear vibration motor, a bar type vibration motor, a coin type vibration motor, or a piezoelectric element vibration motor. For example, if a voice call request is received from another portable apparatus (not shown), the vibration motor 164 may operate under control of the controller 110 in the portable apparatus 100 that is in a vibration mode.

One vibration motor 164 or two or more vibration motors 164 may be located in the portable apparatus 100. The vibration motor 164 may also vibrate a whole part of the portable apparatus 100 or may locally vibrate a part of the portable apparatus 100.

According to an embodiment of the present disclosure, the vibration motor 164 may output a haptic feedback corresponding to a content changed in response to an increase in a visual fatigue. For example, the vibration motor 164 may receive EEG information from the wearable apparatus 200 and analyze the received EEG information to output a haptic feedback corresponding to a content changed in a response to an increase in a visual fatigue under control of the controller 110. The vibration motor 164 may also provide various types of haptic feedbacks (e.g., a strength and a duration time of vibrations) that are pre-stored or received from an external source based on a control command of the controller 110.

The connector 165 may be used as an interface for connecting the portable apparatus 100 to an external apparatus (not shown) or a power source (not shown).

The portable apparatus 100 may transmit data (or a content) stored in the storage unit 175 to an external source through a wired cable connected to the connector 165 or receive the data (or the content) from the external source through the wired cable under control of the controller 110. The portable apparatus 100 may receive power from a power source (not shown) through a wired cable connected to the connector 165 or charge a battery (not shown) from the power source through the wired cable under control of the controller 110. The portable apparatus 100 may also be connected to an accessory (e.g., a speaker (not shown) and a keyboard dock (not shown)) through the connector 165.

The keypad 166 may receive a key input from the user to control the portable apparatus 100. The keypad 166 includes a physical keypad (not shown) formed in a front surface of the portable apparatus 100, a virtual keypad (not shown) displayed in the touch screen 190, and a physical keypad (not shown) that is connectable by wireless or wired. It will be easily understood by those skilled in the art that the physical keypad formed in the front surface of the portable apparatus 100 may be excluded according to a performance or a structure of the portable apparatus 100.

The input pen 167 may touch (or select) an object (e.g., a menu, a text, an image, a video, a figure, an icon, or a shortcut icon) displayed on (or configuring) a screen (e.g., a memo screen, a notepad screen, a calendar screen, or the like) displayed on the touch screen 190 or a handwriting and/or drawing application of the portable apparatus 100 by the user.

The input pen 167 may touch or select a content (e.g., a text file, an image file, an audio file, a video file, or a webpage) displayed on a screen (e.g., a memo screen, a note screen, a calendar screen, or the like) displayed on the touch screen 190 or a handwriting and/or drawing application of the portable apparatus 100 by the user.

The input pen 167 may perform handwriting or drawing (painting or sketching) on a screen of a handwriting or drawing application displayed on the touch screen 190 of the portable apparatus 100 by the user.

The input pen 167 may touch a capacitive type, resistive type, or electromagnetic resonance (EMR) type touch screen or may input letters or the like by using a displayed virtual keypad. The input pen 167 may include a stylus pen or a haptic pen where an embedded vibration device (e.g., an actuator or a vibration motor) vibrates. The input pen 167 may also operate (e.g., vibrate) the vibration device in response to control information received from the portable apparatus 100 and sensing information sensed by a sensor (e.g., an acceleration sensor (not shown)) embedded in the input pen 167.

If the input pen 167 is taken from an insertion hole (not shown), the controller 110 may execute a set handwriting and/or drawing application to display a screen (not shown) of the handwriting and/or drawing application on the touch screen 190.

The input pen 167 may include a finger (e.g., including a thumb) of the user. For example, handwriting or drawing may be input by the user in an application displayed on a capacitive type or resistive type touch screen.

If handwriting or drawing is input by a finger of the user in an application displayed on a capacitive type or resistive type touch screen, the controller 110 may detect one touch of fingers including a thumb by using the touch screen 190 and the touch screen controller 195.

It will be easily understood by those skilled in the art that a shape of the insertion hole (not shown) of the portable apparatus 100 and/or a shape (e.g., a circular cross-section or a polygonal cross-section) or a structure (e.g., a battery (not shown)) of the input pen 167 may be changed according to a performance or a structure of the portable apparatus 100.

The sensor unit 170 may detect a status of the portable apparatus 100 and/or a surrounding status of the portable apparatus 100. The sensor unit 170 may include one sensor or a plurality of sensors. For example, the sensor unit 170 may include a proximity sensor 171 that detects a proximity of the user to the portable apparatus 100, an illumination sensor 172 that detects an amount of light around the portable apparatus 100, and a gyro sensor 173 that detects a direction of the portable apparatus 100 by using rotational inertia of the portable apparatus 100. The sensor unit 170 may also include an acceleration sensor that detects an acceleration of a triaxis (e.g., x, y, and z axes) applied to the portable apparatus 100, a gravity sensor that detects an action direction of gravity, or an altimeter that measures a pressure of air to detect an altitude.

The sensor unit 170 may measure a motion acceleration and a gravity acceleration of the portable apparatus 100. If the portable apparatus 100 does not move, the sensor unit 170 may measure only the gravity acceleration. The sensor unit 170 may further include a fingerprint sensor (not shown) that detects a fingerprint of the user or a heart rate sensor that detects a heartbeat of the user.

At least one sensor included in the sensor unit 170 detects a status of the portable apparatus 100, generates an electrical signal corresponding to the detection, and transmits the electrical signal to the controller 110. It will be easily understood by those skilled in the art that a sensor included in the sensor unit 170 may be added, changed, or deleted according to a performance of the portable apparatus 100.

The storage unit 175 may store signals or data that are input and/or output in response to operations of the mobile communicator 120, the sub communicator 130, the multimedia unit 140, the camera 150, the GPS 155, the I/O unit 160, the sensor unit 170, and the touch screen 190 under control of the controller 110. The storage unit 175 may store a GUI related to a control program for controlling the portable apparatus 100 or the controller 110 and an application provided by a manufacturer or downloaded from an external source, images for providing the GUI, user information, documents, databases (DBs), or pieces of related data.

The storage unit 175 according to an embodiment of the present disclosure may store portable apparatus information, wearable apparatus information, or server information.

The storage unit 175 may store received wearable apparatus status information.

The storage unit 175 may store first through third touches, first through third touch locations, and first through third touch location information.

The storage unit 175 may store a visual feedback (e.g., a video source or the like) that is output from the touch screen 190 in response to an increase in a visual fatigue and is recognizable by the user, an auditory feedback (e.g., a sound source or the like) that is output from the speaker 163 and is recognizable by the user, and a haptic feedback (e.g., a haptic pattern or the like) that is output from the vibration motor 164 and is recognizable by the user.

The storage unit 175 may store a feedback providing time (e.g., 300 msec) of a feedback provided to the user.

The term "storage unit" used herein includes the storage unit 175, the ROM 112 or the RAM 113 of the controller 110, or a memory card (not shown) (e.g., a micro secure digital (SD) card, a memory stick, or the like) installed in the portable apparatus 100. The storage unit may include a nonvolatile memory, a volatile memory, a hard disk drive (HDD), or a solid state drive (SSD).

The power supply unit 180 may supply power to elements 120 through 195 located in the portable apparatus 100 under control of the controller 110. The power supply unit 180 may supply elements of the portable apparatus 100 with power, which is input from a power source (not shown) through a wired cable (not shown) connected to the connector 165, under control of the controller 110. The power supply unit 180 may also supply power to one battery or two or more batteries (not shown) to charge the one battery or the two or more batteries under control of the controller 110. The one battery or the two or more batteries may be located between the touch screen 190 located in the front surface 100a and the back surface.

The power supply unit 180 may wirelessly charge one battery or two or more batteries (not shown) (e.g., according to a magnetic resonance method, an electromagnetic wave method, or a magnetic induction method) under control of the controller 110.

The touch screen 190 includes a touch panel (not shown) that receives a touch input and a display panel (not shown) that displays a screen. The touch screen 190 may provide the user with GUIs corresponding to various types of services (e.g., a voice call, a video call, a data transmission, a broadcast reception, photo capturing, a moving image view, an application execution, etc.). The touch screen 190 transmits an analog signal, which corresponds to a single touch or a multi touch input through the home screen 191 or a GUI, to the touch screen controller 195. The touch screen 190 may receive a single touch or a multi touch through a body of the user (e.g., fingers including a thumb) or the input pen 167.

The display panel (not shown) includes a plurality of pixels and displays an image through the plurality of pixels. For example, the display panel may include a liquid crystal display (LCD), an LED, an OLED, or the like. The display panel may display various operation statuses of the portable apparatus 100, and various types of images and a plurality of objects depending on an execution of an application or a service.

In various embodiments of the present disclosure, a touch is not limited to a touch of the body of the user or the input pen 167 on the touch screen 190 but includes a non-touch of the body of the user or the input pen 167 on the touch screen 190. For example, the non-touch may include hovering where a distance between the touch screen 190 and the body of the user or the input pen 167 is lower than or equal to 50 mm. It will be easily understood by those skilled in the art that a non-touch distance detectable from the touch screen 190 may be changed according to a performance or a structure of the portable apparatus 100.

The touch screen 190 may, for example, be realized as a resistive type, a capacitive type, an infrared type, or an acoustic wave type.

The touch screen 190 may include an EMR type. The EMR type touch screen may further include an additional EMR type touch panel (not shown) that receives an input of an input pen (not shown) having a resonance circuit resonating in an EMR type loop coil.

The touch screen 190 according to an embodiment of the present disclosure may output a visual feedback corresponding to a content changed in response to an increase in a visual fatigue. The touch screen 190 may receive EEG information from the wearable apparatus 200 and analyze the received EEG information to display a visual feedback corresponding to a content changed in response to an increase in a visual fatigue under control of the controller 110.

In the various embodiments of the present disclosure, a display unit may include the touch screen 190.

The touch screen controller 195 converts an analog signal corresponding to a single touch or a multi touch, which is received from the touch screen 190, into a digital signal and transmits the digital signal to the controller 110. The controller 110 may calculate X coordinates and Y coordinates corresponding to a touch location on the touch screen 190 by using the digital signal received from the touch screen controller 195.

The controller110 may control the touch screen 190 by using the digital signal received from the touch screen controller 195. For example, the controller 110 may display a shortcut icon (e.g., denoted by reference numeral 193a of FIG. 5A) displayed on the touch screen 190 so as to enable the shortcut icon 193a to be distinguished from other shortcut icons (e.g., denoted by reference numerals 193b through 193h) or execute an application (e.g., a call) corresponding to the selected shortcut icon 193a of FIG. 5A to display an application screen in response to an input touch.

The touch screen controller 195 may be realized as one touch screen controller 195 or a plurality of touch screen controllers 195. The touch screen controller 195 may be included in the controller 110 according to a performance or a structure of the portable apparatus 100.

The touch screen controller 195 converts an analog signal into a digital signal and transmits the digital signal to the controller 110, wherein the analog signal corresponds to a touch received from an EMR type touch screen separately from an analog signal corresponding to a single touch or a multi touch received from the touch screen 190. The controller 110 may calculate X and Y coordinates corresponding to a touch location on an EMR type touch screen by using the digital signal received from the touch screen controller 195. The EMR type touch screen may also use an EMR type touch screen controller (not shown).

The portable apparatus 100 has been illustrated as including only one touch screen in FIGS. 1 and 2 but may include a plurality of touch screens. The plurality of touch screens may be respectively located in housings (not shown), and the housings may be connected to one another by a hinge (not shown). Also, a plurality of flexible touch screens may be located in one housing (not shown). The plurality of flexible touch screens may include one display panel and a plurality of touch panels. The plurality of flexible touch screens may include one touch panel corresponding to a plurality of display panels. The plurality of flexible touch screens may also include a plurality of touch panels corresponding to a plurality of display panels.

It will be easily understood by those skilled in the art that at least one element of the portable apparatus 100 of FIG. 2 may be added, delete, or changed in response to a performance of the portable apparatus 100.

Referring to FIGS. 1 and 2, the wearable apparatus 200 may be connected to the portable apparatus 100 or the server 300 by wire or wirelessly by using a communicator 230.

The wearable apparatus 200 according to an embodiment of the present disclosure may refer to an apparatus that may detect bio-information (e.g., EEG of the user). For example, the bio-information of the user may include EEG, a body temperature, a heartbeat, a pulse rate variation, a blood pressure, a blood glucose, breath information, an oxygen saturation, a skin state, a motion amount, stress, a stress index, sleep information, etc. Also, the wearable apparatus 200 may refer to an apparatus that may transmit detected EEG to the portable apparatus 100 and/or the server 300. For example, the wearable apparatus 200 that detects the EEG of the user may include a headband type wearable apparatus, a cap type wearable apparatus, a hat type wearable apparatus, a headset type wearable apparatus, a headphone type wearable apparatus, or the like.

The wearable apparatus 200 may be connected to the portable apparatus 100 or the server 300 by using the communicator 230. The wearable apparatus 200 may detect EEG of the user by using a touch type or a non-touch type sensor 270 under control of a controller 210.

The wearable apparatus 200 may include the controller 210, the communicator 230, an I/O unit 260, the sensor 270, a storage unit 275, a battery 280, and a display unit 290.

The controller 210 may include a processor 211, a ROM 212 that stores a control program for controlling the wearable apparatus 200, and a RAM 213 that stores a signal or data input from an outside of the wearable apparatus 200 and is used as a storage area for various types of jobs performed in the wearable apparatus 200.

The controller 210 controls an overall operation of the wearable apparatus 200 and a signal flow between internal elements 220 through 290 of the wearable apparatus 200 and performs a function of processing data. The controller 210 may control the battery 280 to supply power to the internal elements 220 through 290 or interrupt power supplied to the internal elements 220 through 290. Also, if an input of the user or a preset condition is satisfied, the controller 210 may operate the sensor 270.

The processor 211 may include a GPU (not shown) for graphic processing. The processor 211 may be realized as a SoC type including a core (not shown) and a GPU (not shown). The processor 211 may include a single core, a dual core, a triple core, a quad core, and a multiple core. Also, the processor 211, the ROM 212, and the RAM 213 may be connected to one another through a bus.

The controller 210 may control the communicator 230, the I/O unit 260, the sensor 270, the storage unit 275, the battery 280, and the display unit 290.

The controller 210 according to an embodiment of the present disclosure may detect EEG of the user by using the sensor 270 or may detect a status of the wearable apparatus 200 through an additional sensor (not shown).

The controller 210 may transmit EEG information of the user corresponding to the detected EEG of the user to the portable apparatus 100 or the server 300 through the communicator 230.

The controller 210 may control to transmit changed wearable apparatus status information to the portable apparatus 100 by using the communicator 230 and stored portable apparatus information.

The term "controller 210 of the wearable apparatus 200" used herein includes the processor 211, the ROM 212, and the RAM 213.

The communicator 230 may be connected to the portable apparatus 100 or the server 300 by using a wireless LAN 231 and/or a short-range communicator 232. The communicator 230 may transmit the EEG information of the user to the portable apparatus 100 or the server 300 under control of the controller 210.

The communicator 230 may include the wireless LAN 231 and/or the short-range communicator 232. For example, the communicator 230 may include one or both of the wireless LAN 231 and the short-range communicator 232. The communicator 230 may further include wired Ethernet.

The wireless LAN 231 may be wirelessly connected to an AP in an installation place of the AP under control of the controller 210. For example, the wireless LAN 231 may include Wi-Fi. The wireless LAN 231 supports the wireless LAN standard IEEE 802.11x of IEEE. The short-range communicator 232 may wirelessly perform a short-range communication between the portable apparatus 100 and an external apparatus without the AP under control of the controller 210. The short-range communication may include Bluetooth, Bluetooth low energy, IrDA, UWB, an NFC, etc.

The communicator 230 may transmit the EEG of the user detected by (or stored in) the sensor 270 to the portable apparatus 100 or the server 300 under control of the controller 210. The communicator 230 may periodically (e.g., 500 msec that is changeable) transmit the EEG of the user detected by (or stored in) the sensor 270 to the portable apparatus 100 or the server 300 under control of the controller 210. The communicator 230 may also receive a transmission request of the detected (or stored) EEG of the user or wearable apparatus status information from the portable apparatus 100 and/or the server 300.

The wearable apparatus 200 may be connected to another external apparatus (e.g., a wireless speaker, a wireless headset, another user EEG detecting apparatus, or the like) by using the communicator 230.

The wearable apparatus 200 may also include a mobile communicator (not shown). The mobile communicator of the wearable apparatus 200 may transmit and/or receive a wireless signal for a voice call, a video call, an SMS, an MMS, and a data communication with a portable phone (not shown) having a connectable phone number, a smartphone (not shown), a tablet PC, a tablet apparatus, or another portable apparatus (not shown).

The wearable apparatus 200 may include a camera (not shown) capturing a still image or a moving image under control of the controller 210. The camera may be located in a front surface (e.g., a forehead area of the user) of the wearable apparatus 200.

The wearable apparatus 200 may include a GPS (not shown). The wearable apparatus 200 may calculate a current location of an outdoor wearable apparatus 200 by using the GPS and calculate a location of an indoor wearable apparatus 200 by using an AP.

The I/O unit 260 may include at least one selected from one button or two or more buttons (not shown), a microphone (not shown), a speaker (not shown), a vibration motor (not shown), and a connector (not shown).

The button (not shown) includes a power button. The button may include a volume button (not shown) or a back button (not shown). The button may also include a touch button.

The microphone (not shown) receives a voice or a sound from an external source to generate an electrical signal under control of the controller 210.

The speaker (not shown) may output a sound corresponding to a function or an operation performed in the wearable apparatus 200 under control of the controller 210.

The vibration motor (not shown) may output a vibration corresponding to a function or an operation performed in the wearable apparatus 200 under control of the controller 210.

The connector (not shown) may transmit data (e.g., EEG of the user or the like) stored in the storage unit 275 of the wearable apparatus 200 to an external source or may charge the battery 280 under control of the controller 210.

The sensor 270 may detect EEG of the user under control of the controller 210. The sensor 270 may include a plurality of electrodes. The sensor unit 270 may detect the EEG through the plurality of electrodes. A material of the electrodes may include a conductive fiber (e.g., a silver fiber), a conductive polymer (e.g., polyethylene, polyparaphenylene, polyphenol, polyaniline, or the like), or a metal coated with highly conductive metal. The sensor unit 270 may detect a potential difference occurring from the plurality of electrodes. An EEG measurement may be similar to a voltage measurement having a very large impedance (e.g., a high resistance). EEG data detected by the sensor 270 may be transmitted to the controller 210. For example, the EEG data may include analog data that is raw data or digital data that is acquired by processing raw data. The detected EEG data may be stored in the storage unit 275 under control of the controller 210.

EEG of the user may refer to a current that appears according to a brain activity or waveforms that are acquired by driving, amplifying, and recording the current. Types of EEG vibrating in complicated patterns may be classified into a delta ($\delta$) wave between 0.2 Hz and 3.99 Hz, a theta ($\theta$) wave between 4 Hz and 7.99 Hz, an alpha ($\alpha$) wave between 8 Hz and 12 Hz, a beta ($\beta$) wave between 13 Hz and 29.99 Hz, and a gamma ($\gamma$) wave between 30 Hz and 50 Hz. It will be easily understood by those skilled in the art that a frequency band of the above-described EEG is one embodiment and thus may be changed by a surrounding environment and a detecting apparatus.

The $\delta$ wave may be remarkably detected from a user who is in deep sleep or a newborn baby. The $\theta$ wave may be mainly detected from a child who enters an emotional stability or sleep. The $\alpha$ wave may be mainly detected in a comfortable status such as tension relaxation. The $\beta$ wave may be mainly detected from a frontal region of the user, i.e., may be detected when the user is awake or performs a conscious activity such as speaking. The ($\gamma$) wave may vibrate faster than the ($\beta$) wave and may be detected when the user is in an impatient state or processes high-level cognitive information.

The sensor 270 may also detect an internal status or an external status of the wearable apparatus 200. Also, the sensor 270 may detect a change in the internal status or the external status of the wearable apparatus 200 under control of the controller 210. For example, the sensor 270 may include an acceleration sensor (not shown) that detects an acceleration of tri-axis (e.g., x, y, and z axes) applied to the wearable apparatus 200 or a gyro sensor (not shown) that detects a direction of the wearable apparatus 200 by using rotational inertia of the wearable apparatus 200. It will be easily understood by those skilled in the art that a sensor included in the sensor 270 may be added, changed, or deleted according to a performance of the wearable apparatus 200.

The storage unit 275 may store signals or data that are input and/or output to correspond to operations of the communicator 230, the I/O unit 260, the sensor 270, and the display unit 290 under control of the controller 210. The storage unit 275 may store a GUI related to a control program for controlling the wearable apparatus 200 or the controller 210 and an application provided by a manufacturer or downloaded from an external source, images for providing the GUI, user information, documents, DBs, or pieces of related data.

The storage unit 275 may store data related to an operation of the wearable apparatus 200 or environment information (e.g., a temperature, an acceleration, an illumination intensity, or the like) or status information (e.g. power on, an operation, or the like) detected by the sensor 270 under control of the controller 210.

The storage unit 275 may store EEG data detected by the sensor 270.

The storage unit 275 may store EEG information of the user including at least one selected from raw data and digital data.

The storage unit 275 may store wearable apparatus information corresponding to the wearable apparatus 200, portable apparatus information corresponding to the portable apparatus 100, or server information corresponding to the server 300. For example, it will be easily understood by those skilled in the art that apparatus information may include a plurality of items indicating an identification (ID) for a history management, an apparatus ID, an apparatus name, an apparatus URI, and an apparatus status but may include items indicating various statuses of an apparatus without being limited thereto.

The battery 280 may supply power to internal elements 230 through 290 of the wearable apparatus 200 under control of the controller 210. A power supply unit (not shown) may supply the wearable apparatus 200 with power that is input from an external power source (not shown) through a wired cable (not shown) connected to a connector (not shown) under control of the controller 210. The power supply unit may also charge the one battery 280 or two or more batteries 280 with power that is supplied under control of the controller 210.

The power supply unit may wirelessly (e.g., according to a magnetic resonance method, an electromagnetic method, or a magnetic induction method) charge one battery 280 or two or more batteries 280 under control of the controller 210.

The display unit 290 may provide the user with a GUI corresponding to various types of services (e.g., a voice call, a video call, a data transmission, a broadcast reception, photo capturing, a moving image view, an application execution, etc.) under control of the controller 210. A display panel (not shown) includes a plurality of pixels and displays an image through the pixels. For example, the display panel may be realized as an LCD, an OLED, an LED, or the like. The display panel may display various types of images and a plurality of objects according to various types of statuses, applications, or service executions of the wearable apparatus 200.

The display unit 290 may include a touch screen (not shown) including a display panel (not shown) and a touch panel (not shown). The touch screen may be realized as a resistive type, a capacitive type, an infrared type, or an acoustic wave type.

According to an embodiment of the present disclosure, the display unit 290 may output a visual feedback corresponding to a user EEG detection under control of the controller 210.

It will be easily understood by those skilled in the art that the portable apparatus 100 and the wearable apparatus 200 are classified in FIGS. 1 and 2, but a plurality of portable apparatuses (e.g., tablet apparatuses 1 and 2) having the same types may be embodied.

It will be easily understood by those skilled in the art that at least one selected from elements of the wearable apparatus 200 shown in FIG. 2 may be added, changed, or deleted according to a performance of the wearable apparatus 200.

Referring to FIG. 2, the server 300 may be connected to at least one selected from the portable apparatus 100 and the wearable apparatus 200 through a communicator (not shown) by a wireless or wired connection. The server 300 may request status information from the wearable apparatus 200. The server 300 may receive status information from the wearable apparatus 200. The server 300 may receive a request corresponding to a transmission of the status information of the wearable apparatus 200 from the portable apparatus 100. The server 300 may transmit the status information of the wearable apparatus 200 to the portable apparatus 100.

In various embodiments of the present disclosure, the server 300 may refer to a computing apparatus that may store EEG data received from the wearable apparatus 200 and transmit the stored EEG data to the portable apparatus 100. The server 300 may refer to a computing apparatus that may store EEG data from the wearable apparatus 200 and calculate a visual fatigue by using the stored EEG data.

The server 300 may also refer to a computing apparatus that may store status information of the wearable apparatus 200 received from the wearable apparatus 200 and transmit the stored status information of the wearable apparatus 200 to the portable apparatus 100. The server 300 may include a gateway (not shown), a home network server (not shown) or a cloud server (not shown). A display apparatus (not shown) or a refrigerator (not shown) may act as the server 300 in a home network environment.

It will be easily understood by those skilled in the art that at least one element of the server 300 of FIGS. 1 and 2 may be added, changed, or deleted according to a performance of the server 300.

Figure 3A:
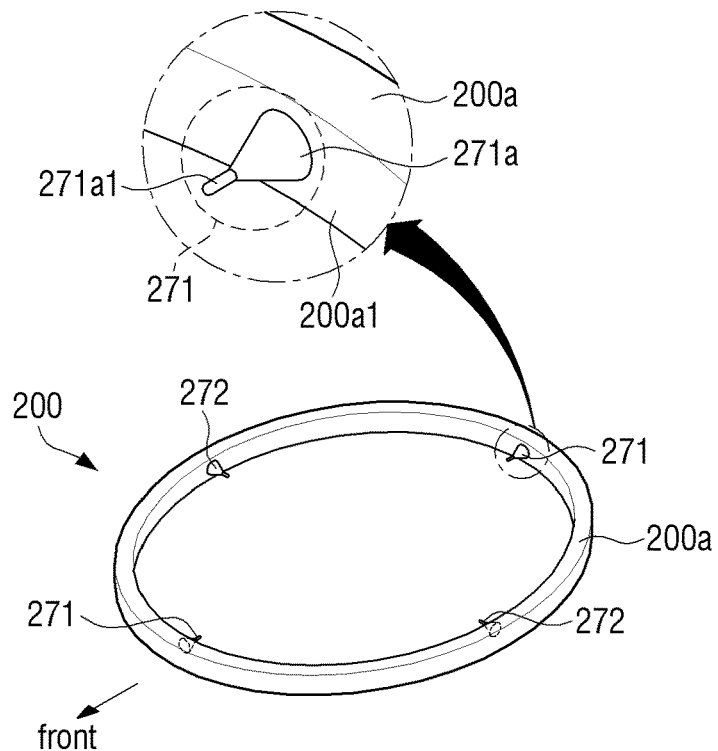
FIGS. 3A and 3B are schematic perspective views of a wearable apparatus according to an embodiment of the present disclosure.
Figure 3B:
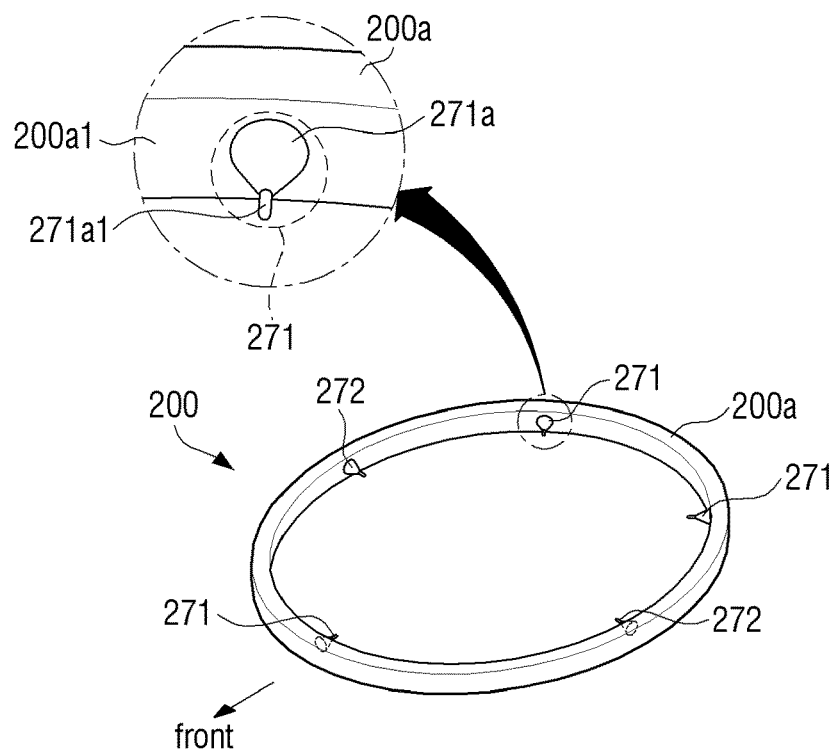

FIGS. 3A and 3B are schematic perspective views of a wearable apparatus according to an embodiment of the present disclosure.

Referring to FIGS. 3A and 3B, the wearable apparatus 200 that is worn on a head of a user may be realized in a ring shape. The ring shape may include a concentric circle or an ellipse. The wearable apparatus 200 may be realized in a polygon having three or more vertexes. The wearable apparatus 200 may also be realized as a headband type wearable apparatus, a headset type wearable apparatus, or a helmet type wearable apparatus. It will be easily understood by those skilled in the art that the wearable apparatus 200 may be realized in various shapes or types besides the above-mentioned types of wearable apparatuses to detect EEG of the user.

A body 200a of the wearable apparatus 200 may be formed of a high molecular compound, metal, fiber, or ceramics. A size (e.g., a diameter) of the body 200a of the wearable apparatus 200 having elasticity may vary according to whether to wear or do not wear the body 200a of the wearable apparatus 200. The wearable apparatus 200 may have various diameters in response to a size of a head of the user. For example, the wearable apparatus 200 may be classified as infant, child, youth, or adult.

Some of the elements 210 through 290 shown in FIG. 2 may be located in the body 200a of the wearable apparatus 200. A button of the I/O unit 260 or the display unit 290 may be exposed to an outside of the body 200a of the wearable apparatus 200. Also, the sensor 270 may be exposed to an outside of the wearable apparatus 200.

One electrode or a plurality of electrodes 271 and 272 may be exposed in an internal side 200a1 of the body 200a in the wearable apparatus 200. The sensor 270 may include a measurement electrode 271 that detects EEG and a reference electrode 272 (e.g., ground). A structure of the measurement electrode 271 and a structure of the reference electrode 272 are the same, and thus their repeated descriptions are omitted.

A material of the measurement electrode 271 may include a conductive fiber (e.g., a silver fiber), conductive polymer (e.g., polyacetylene, polyparaphenelene, polyphenol, polyaniline, or the like), or metal coated with conductive metal.

The measurement electrode 271 may contact a body (e.g., a head) of the user. The measurement electrode 271 may have a base 271a and one protrusion 271a1. The protrusion 271a1 of the measurement electrode 271 may have elasticity.

If the protrusion 271a1 having elasticity contacts the body of the user, the protrusion 271a1 may be bent in response to a movement direction of the wearable apparatus 200. For example, if the wearable apparatus 200 is worn on the user, the protrusion 271a1 may be bent in an opposite direction to the movement direction (e.g., a wearing direction) of the wearable apparatus 200. Also, if the wearable apparatus 200 is separated from the body of the user, the protrusion 271a1 may return to the opposite direction to the movement direction of the wearable apparatus 200.

Locations of the measurement electrode 271 and the reference electrode 272 in the wearable apparatus 200 may vary according to the number of measurement electrodes 271 and the reference electrodes 272 of the wearable apparatus 200. A location of the measurement electrode 271 that measures EEG of the user and a location of the reference electrode 272 may be determined based on an activation degree of a visual cortex and a frontal lobe recognizing and processing the activation degree of the visual cortex.

Table 1 below shows examples of a location of the measurement electrode 271 and a location of the reference electrode 272 corresponding to the number of measurement electrodes 271 in the wearable apparatus 200.

TABLE 1

| Number of Measurement Electrodes | Location of Measurement Electrode | Location of Reference Electrode |
|---|---|---|
| 2 | Central Area of Forehead, Central Area of Back of the Head | Ear Area, Both Ear Areas |
| 3 | Both Areas Based on Central Area of Forehead, Central Area of Back of the Head | Ear Area, Both Ear Areas |

As shown in FIG. 3A, if the number of measurement electrodes 271 is 2, the measurement electrodes 271 may be located in a central area of a forehead (e.g., a frontal bone area or a glabella area corresponding to a frontal lobe) and a central area of a back of the head (e.g., an occipital bone area corresponding to an occipital lobe). The reference electrodes 272 may be located in an ear area (e.g., a temporal bone corresponding to a temporal lobe) or both ear areas.

The locations of the measurement electrodes 271 and the locations of the reference electrodes 272 may intersect with each other (e.g., at an angle between 45° and 135°). Locations of a plurality of measurement electrodes face one another. Also, the reference electrodes 272 face each other. The reference electrodes 272 may intersect with one another (e.g., at an angle between 45° and 135°).

As shown in FIG. 3B, if the number of measurement electrodes 271 is 3, one of the measurement electrodes 271 may be located in the central area of the forehead (e.g., the frontal bone area or the glabella area corresponding to the frontal lobe), and two of the measurement electrodes 271 may be located in the central area of the back of the head (e.g., the occipital area corresponding to the occipital lobe). The reference electrodes 272 may be located in the ear area (e.g., the temporal bone corresponding to the temporal lobe) or both ear areas.

The locations of the measurement electrodes 271 may intersect with the locations of the reference electrodes 272. A plurality of measurement electrodes 271 that are located in the back of the head based on a virtual extension line that is connected from the measurement electrode 271 located in the forehead toward the back of the head may be located at the same intervals (e.g., on left and right sides). Also, locations of a plurality of reference electrodes 272 face one another. The reference electrodes 272 may intersect with one another (e.g., at an angle between 45° and 135°).

If the number of measurement electrodes 271 increases, the measurement electrodes 271 may be located in a top area of the head (e.g., a parietal bone area corresponding to a parietal lobe).

It will be easily understood by those skilled in the art that Table 1 above does not limit the number of measurement electrodes 271, locations of the measurement electrodes 271, and locations of the reference electrodes 272 to the above-described items but may indicate various combinations of locations of the measurement electrodes 271 and locations of the reference electrodes 272 corresponding to the number of measurement electrodes 271.

Figure 4:
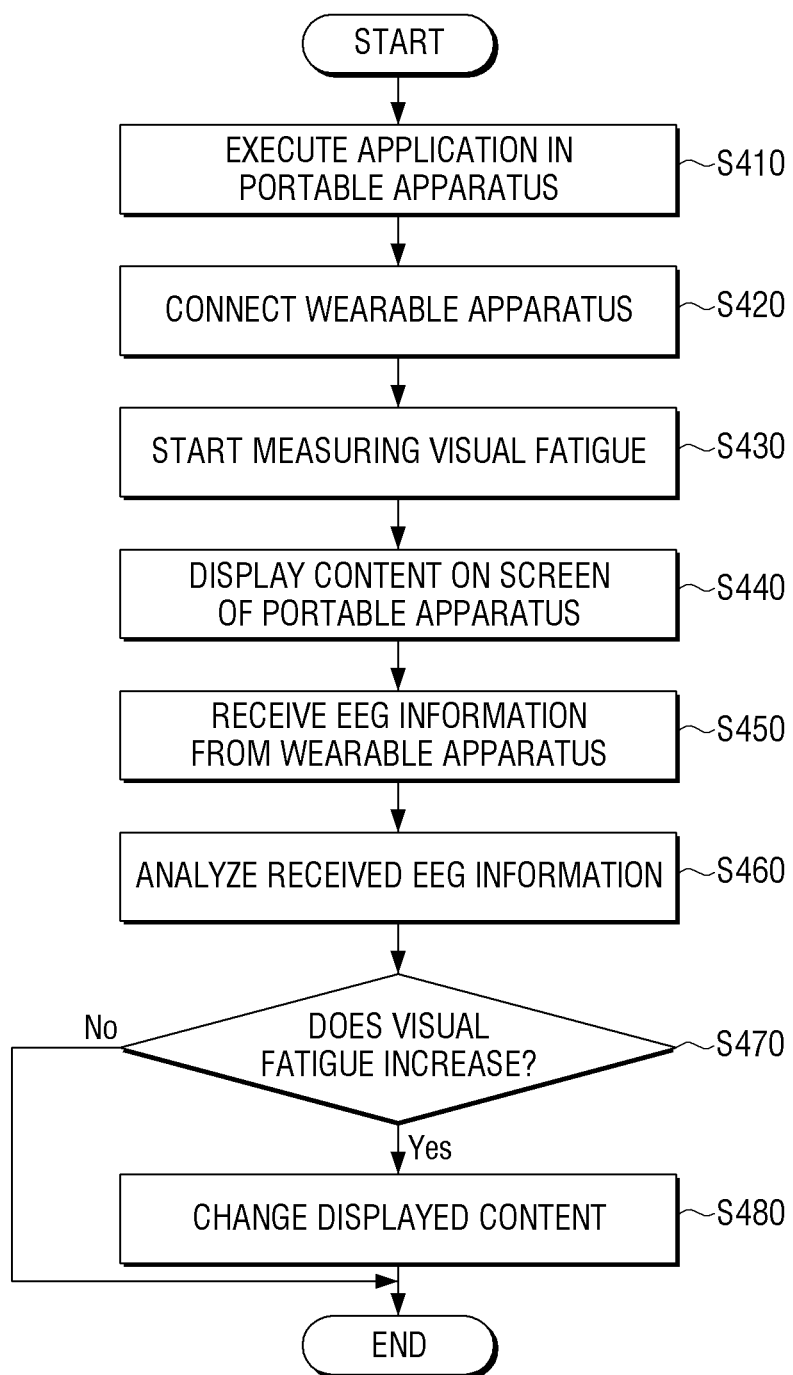
FIG. 4 is a schematic flowchart of a method of changing a content screen of a portable apparatus according to an embodiment of the present disclosure.

FIG. 4 is a schematic flowchart of a method of changing a content screen of a portable apparatus according to an embodiment of the present disclosure.

FIGS. 5A to 12B illustrate a screen of a portable apparatus according to various embodiments of the present disclosure.

Referring to FIG. 4, an application is executed in the portable apparatus in operation S410.

Referring to FIG. 5A, the portable apparatus 100 may display an application (e.g., corresponding to shortcut icons 193a through 193i) or a widget 194 on a home screen 191 distinguished from a status bar 192. Also, a user wears the wearable apparatus 200. For example, the wearable apparatus 200 may be worn on a head of the user.

The user may perform a first touch (501) on the shortcut icon 193g corresponding to a visual fatigue application (e.g., Smart-eye) that is a selection target of the shortcut icons 193a through 193i displayed on a screen of the portable apparatus 100. It will be easily understood by those skilled in the art that a calculation of a visual fatigue of a user may be embodied as a visual fatigue calculation application, a visual fatigue OS, or visual fatigue calculation middleware.

The controller 110 may detect the first touch 501 by using the touch screen 190 and the touch screen controller 195. The controller 110 may calculate a first touch location 501a (e.g., X1 and Y1 coordinates) corresponding to the first touch 501 by using an electrical signal received from the touch screen controller 195.

The controller 110 may store first touch location information corresponding to the first touch location 501 in the storage unit 175. The stored first touch location information may include a touch ID for a history management, a touch location, a touch detection time, or touch information (e.g., a touch pressure, a touch direction, a touch duration time, or the like).

The controller 110 may also or alternatively detect a first hovering (not shown) by using the touch screen 190 and the touch screen controller 195. The controller 110 may calculate a first hovering location (not shown) (e.g., X11 and Y11 coordinates) corresponding to the first hovering by using an electrical signal received from the touch screen controller 195.

The controller 110 may store first hovering location information corresponding to the first hovering location in the storage unit 175. The stored first hovering location information may include a hovering ID for a history management, a hovering detection location, a hovering detection time, or hovering information (e.g., a hovering height h, a hovering direction, a hovering duration time, or the like).

A touch of the input pen 167 is a single point touch. The controller 110 may detect the touch of the input pen 167 as the single point touch. Also, the controller 110 may determine a touch of an EMR type input pen (not shown) through a second touch panel (not shown). The controller 110 may determine a touch of an input pen (e.g., a capacitive type input pen), which is not an EMR type, according to a single point touch.

Figure 5B:
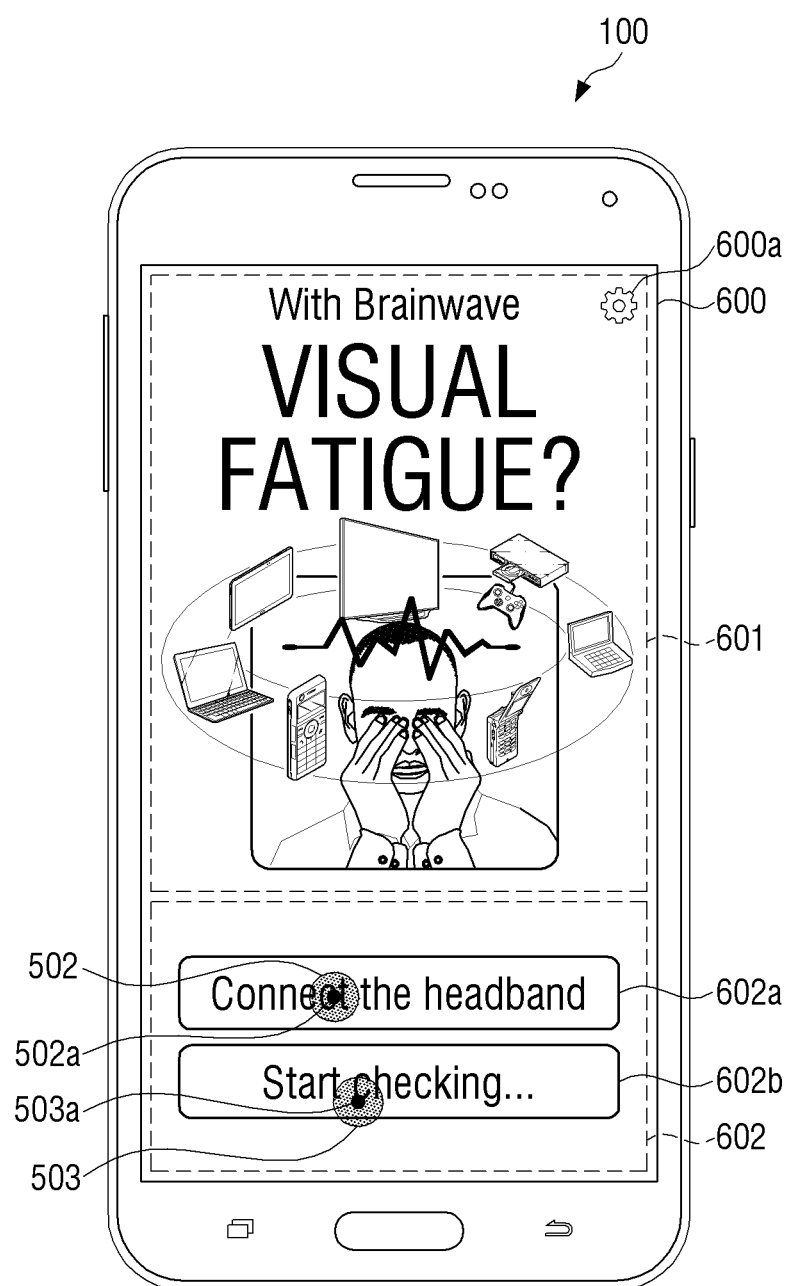

Referring to FIG. 5B, the controller 110 of the portable apparatus 100 may display an application (e.g., Smart-eye) screen 600 corresponding to the first touch 501 on a screen of the portable apparatus 100. The application screen 600 displayed to correspond to the first touch 501 may include a home screen of an application.

The home screen 600 of the application may include may include an introduction area 601 that introduces the application (e.g., Smart-eye) and an interaction area 602 that receives an interaction (e.g., a touch, a touch gesture input, or the like) between the application and the user. The interaction area 602 may display a button 602a corresponding to "connect the headband" and/or a button 602b corresponding to "start checking EEG . . . " corresponding to a visual fatigue.

Figure 12A:
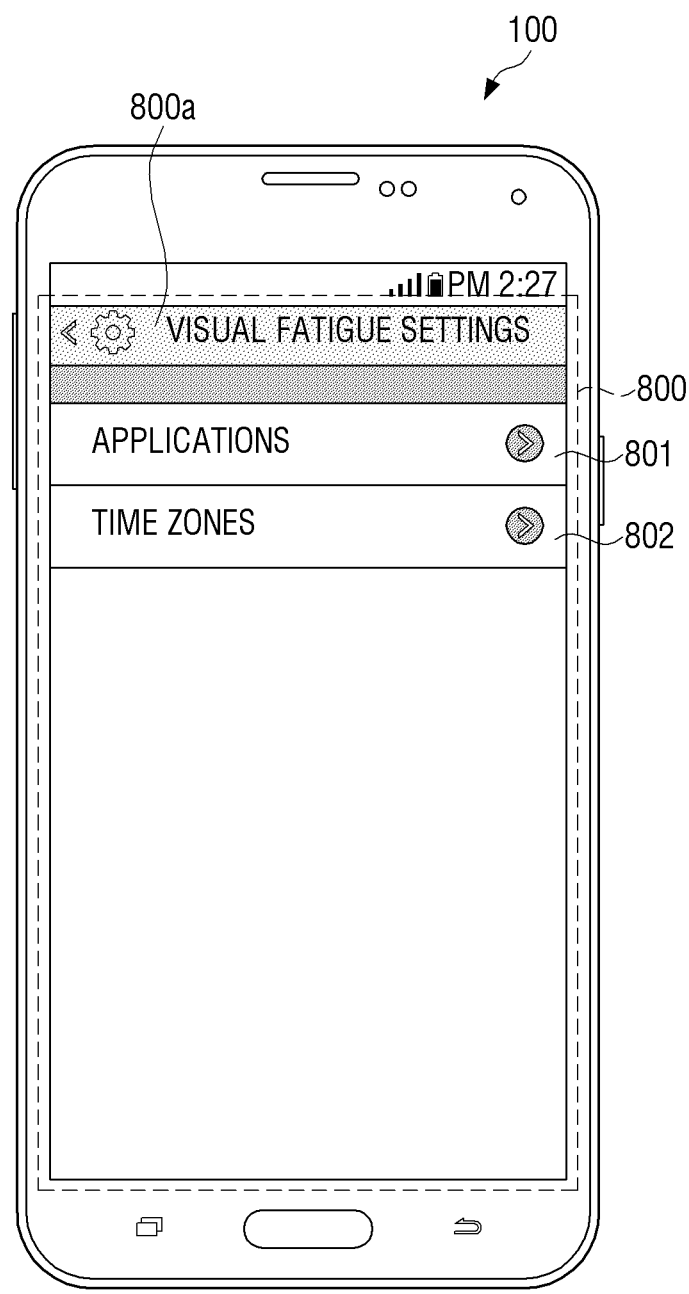
FIG. 12A to 12C illustrate an environment setting screen of a portable apparatus according to various embodiments of the present disclosure.
Figure 12B:
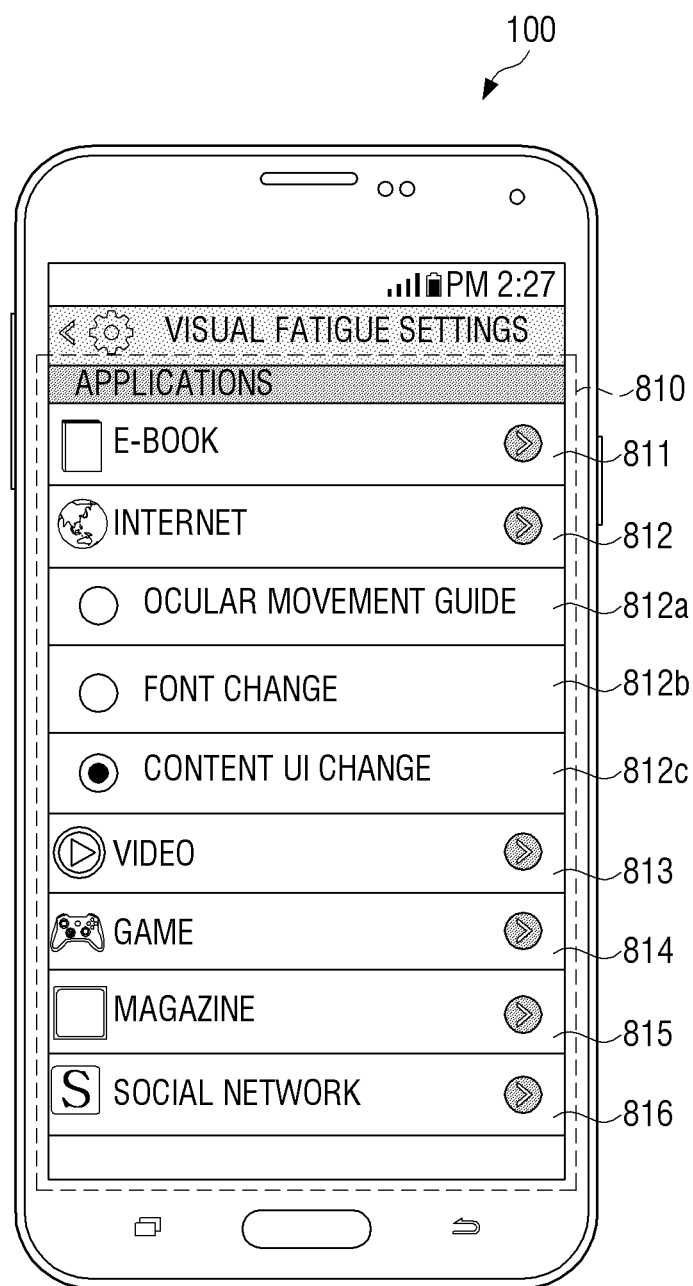
Figure 12C:
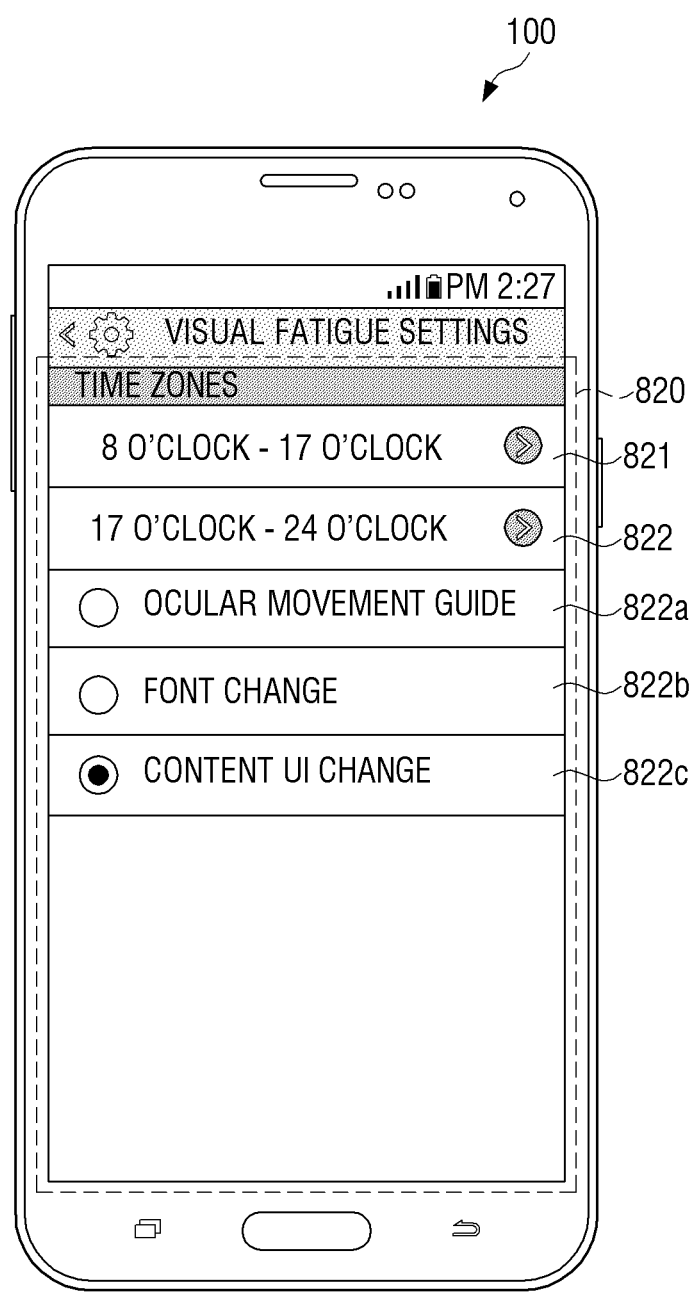

FIGS. 12A to 12C illustrate an environment setting screen of a portable apparatus according to an embodiment of the present disclosure.

Referring to FIGS. 12A to 12C, if a user selects a shortcut icon 600a corresponding to an environment setting located on a top of the home screen 600 of the application, the controller 110 may display an environment setting screen 800 as shown in FIG. 12A. If the user selects the shortcut icon 600a, the controller 110 may change the home screen 600 of the application into the environment setting screen 800 corresponding to a visual fatigue.

Visual fatigue settings menu 800a displayed on the environment setting screen 800 may include selections to address visual fatigue related to an application 801, which addresses a visual fatigue according to each application, or related to a time zone 802, which addresses a visual fatigue according to time. It will be easily understood by those skilled in the art that the items displayed on the environment setting screen 800 may be changed or deleted according to a function and/or a performance of the portable apparatus 100.

If the user selects the application 801 that is a menu for setting the visual fatigue according to applications, the controller 110 may display a visual fatigue setting screen 810 according to each application.

FIG. 12B illustrates an example of the visual fatigue setting screen 810 according to each application. Referring to FIG. 12B, items displayed on the visual fatigue setting screen 810 according to each application may include an e-book 811, a web browser 812, a video player 813, a game 814, a magazine 815, or a social network system 816. The user may select the items 811 through 816 and set a detailed environment to be provided in the event of visual fatigue. For example, if the user selects the web browser 812, the user may set a detailed visual fatigue environment of the web browser 812. The setting of the detailed visual fatigue environment of the web browser 812 may include an ocular movement guide 812a, a font change 812b, and a content UI change 812c. The setting of the detailed visual fatigue environment of the web browser 812 may further include a color screen (e.g., a color filter) control, a luminance control, a color control, a chroma control, etc.

It will be easily understood by those skilled in the art that items (e.g., applications 811 through 816 or visual fatigue corresponding items 812a through 812c) displayed on the visual fatigue setting screen 810 according to each application may be added, changed, or deleted according to a function and/or a performance of the portable apparatus 100.

If the user selects the time zone 802, the controller 110 may display a visual fatigue setting screen 820 according to each time zone. FIG. 12C illustrates an example of a visual fatigue setting screen 820 for setting a visual fatigue according to time zone. Referring to FIG. 12C, items displayed on the visual fatigue setting screen 820 according to each time zone may include a time zone 821 between 8 o'clock and 17 o'clock and a time zone 822 between 17 o'clock and 24 o'clock. The user may select the items 821 and 822 and set a detailed environment. For example, if the user selects the time zone 822 between 17 o'clock and 24 o'clock, the user may set a detailed visual fatigue environment of the time zone 822 between 17 o'clock and 24 o'clock. The setting of the detailed visual fatigue environment of the time zone between 17 o'clock and 24 o'clock may include an ocular movement guide 822a, a font change 822b, and a content UI change 822c.

It will be easily understood by those skilled in the art that the items (e.g., the time zones 821 and 822) displayed on the visual fatigue setting screen 820 according to each time zone and the items 822a through 822c corresponding to a visual fatigue may be added, changed, or deleted according to a function and/or a performance of the portable apparatus 100.

In operation S420 of FIG. 4, a wearable apparatus is connected.

Referring to FIG. 5B, the user may perform a second touch 502 on the button 602a corresponding to "connect the headband" on the hone screen 600 of the application (e.g., Smart-eye).

The controller 110 may detect the second touch 502 by using the touch screen 190 and the touch screen controller 195. The controller 110 may calculate a second touch location 502a (e.g., X2 and Y2 coordinates) corresponding to the second touch 502 by using an electrical signal received from the touch screen controller 195.

The controller 110 may store second touch location information corresponding to the second touch location 502a in the storage unit 175. The stored second touch location information may include a touch ID for a history management, a touch location, a touch detection time, or touch information (e.g., a touch pressure, a touch direction, a touch duration time, or the like).

A detection of a second hovering performed in operation S420 of FIG. 4 is similar to a detection of first hovering performed in operation S410 of FIG. 4, and thus a repeated description thereof is omitted.

The controller 110 of the portable apparatus 100 may search for the wearable apparatus 200 around the portable apparatus 100 by using a communicator. The wearable apparatus 200 that is a connection target may be selected from a search list (not shown) corresponding to a search result of a wearable apparatus displayed on the screen of the portable apparatus 100. The wearable apparatus 200 that is the connection target may be selected by the user or the controller 110. If only the wearable apparatus 200 that is the connection target is searched from the search list, the controller 110 may select the wearable apparatus 200 that is the connection target without a user input.

The controller 110 of the portable apparatus 100 may be connected to a communicator of the wearable apparatus 200 through a first wireless communication by using a communicator in response to the selection. For example, the first wireless communication may be a wireless communication (e.g., a short-range communication) having a limited transmission distance (e.g., a distance lower than or equal to 1 m, lower than or equal to 50 m, or lower than or equal to 100 m). The portable apparatus 100 and the wearable apparatus 200 may be connected to each other through the first wireless communication having the limited transmission distance. The first wireless communication may be a short-range wireless communication but is not limited thereto. A second wireless communication may be a long-range wireless communication, e.g., may be a mobile communication, but is not limited thereto.

If the portable apparatus 100 and the wearable apparatus 200 are connected to each other through Bluetooth that is one of first wireless communications, the portable apparatus 100 and the wearable apparatus 200 may be connected to each other through a mutual support profile (e.g, a serial port profile (SPP), an advanced audio distribution profile (A2DP), an audio/video remote control profile (AVRCP), or a hands-free profile (HFP)). Also, the portable apparatus 100 and the wearable apparatus 200 may be connected to each other through Wi-Fi that is one of first wireless communications. It will be easily understood by those skilled in the art that the above-described profile is only an example, and a profile mutually supporting the portable apparatus 100 and the wearable apparatus 200 may be added, changed, or deleted.

If the portable apparatus 100 and the wearable apparatus 200 are connected to each other, the controller 110 of the portable apparatus 100 may store wearable apparatus information received from the wearable apparatus 200 in the storage unit 175. The stored wearable apparatus information may include wireless connection information (e.g., a subsystem identification (SSID), an Internet protocol (IP) address, an media access control (MAC) address, a channel number, a security key, or the like), a product name of the wearable apparatus 200, an ID of the wearable apparatus 200, an MAC address of the wearable apparatus 200, a type of the wearable apparatus 200, a profile of the wearable apparatus 200, a communication method of the wearable apparatus 200, etc.

If the portable apparatus 100 and the wearable apparatus 200 are connected to each other, the controller 210 of the wearable apparatus 200 may store portable apparatus information received from the portable apparatus 100 in the storage unit 275. The portable apparatus information stored in the storage unit 275 of the wearable apparatus 200 is similar to the wearable apparatus information stored in the storage unit 175 of the portable apparatus 100, and thus a repeated description thereof is omitted.

If the portable apparatus 100 and the wearable apparatus 200 are connected to each other, the controller 110 of the portable apparatus 100 may request a current status from the wearable apparatus 200. The current status of the wearable apparatus 200 may include an operation status (e.g., a working or busy status), a standby status, a sleep status, or a hold status.

In various embodiments of the present disclosure, the current status of the wearable apparatus 200 may be the standby status.

The controller 210 of the wearable apparatus 200 may transmit wearable apparatus status information to the portable apparatus 100 through the communicator 230 in response to a request. The controller 110 of the portable apparatus 100 may store the received wearable apparatus status information in the storage unit 175.

If the portable apparatus 100 and the wearable apparatus 200 are connected to each other, the controller 110 of the portable apparatus 100 may display the home screen 600 of the application.

According to an embodiment of the present disclosure, the controller 210 of the wearable apparatus 200 that is turned on may search for the portable apparatus 100 around the wearable apparatus 200 by using the communicator 230. The portable apparatus 100 may be selected from a search list (not shown) corresponding to a search result of the portable apparatus 100 displayed on the display unit 290 of the wearable apparatus 200. The portable apparatus 100 that is a connection target may be selected by the user or the controller 210. If only the portable apparatus 100 that is the connection target is searched from the displayed search list, the controller 210 may select the portable apparatus 100 that is the connection target without a user input.

The controller 210 of the wearable apparatus 200 may be wirelessly connected to a communicator of the portable apparatus 100 by using the communicator 230 in response to the selection.

If the portable apparatus 100 and the wearable apparatus 200 are connected to each other, the controller 210 of the wearable apparatus 200 may store portable apparatus information received from the portable apparatus 100 in the storage unit 275. The stored portable apparatus information may include wireless connection information (e.g., an SSID, an IP address, a channel number, a security key, or the like), a product name of the portable apparatus 100, an ID of the portable apparatus 100, an MAC address of the portable apparatus 100, a type of the portable apparatus 100, a profile of the portable apparatus 100, a communication method of the portable apparatus 100, etc.

In operation S430 of FIG. 4, the measuring of a visual fatigue starts.

A method of measuring and calculating the visual fatigue will be described in greater detail later.

Referring to FIG. 5B, the user may perform a third touch 503 on the button 602b corresponding to "start checking a visual fatigue . . . " on the home screen 600 of the application (e.g., Smart-eye).

The controller 110 may detect the third touch 503 by using the touch screen 190 and the touch screen controller 195. The controller 110 may calculate a third touch location 503a (e.g., X3 and Y3 coordinates) corresponding to the third touch 503 by using an electrical signal received from the touch screen controller 195.

The controller 110 may store third touch location information corresponding to the third touch location 503a in the storage unit 175. The stored third touch location information may include a touch ID for a history management, a touch location, a touch detection time, or touch information (e.g., a touch pressure, a touch direction, a touch duration time, or the like).

A detection of a third hovering performed in operation S430 of FIG. 4 is similar to the detection of the first hovering performed in operation S410 of FIG. 4, and thus a repeated description thereof is omitted.

The controller 110 may request a measurement of EEG of the user from the wearable apparatus 200 in response to a third touch. If the third touch is detected, the controller 110 may generate a control command (e.g., a control packet) corresponding to the measurement of the EEG of the user.

The controller 110 may transmit the generated control command to the wearable apparatus 200 through a communicator. The control command transmitted to the wearable apparatus 200 through the communicator may have a hierarchical structure.

The control packet corresponding to the control command may include three frames including a MAC header (not shown) corresponding to an address and a length of a receiver (e.g., a wearable apparatus), a payload (not shown) corresponding to an EEG measurement request of the wearable apparatus 200, and a cyclical redundancy check (CRC) (not shown) corresponding to a transmission error detection.

The storage unit 175 may store the control command, which is generated corresponding to a user EEG measurement request from the wearable apparatus 200, under control of the controller 110.

The controller 210 of the wearable apparatus 200 may receive the control command corresponding to the user EEG measurement request transmitted from the portable apparatus 100. The received control command may be stored in the storage unit 275 under control of the controller 210.

The controller 210 of the wearable apparatus 200 may start measuring EEG of the user in response to the received control command. The controller 210 of the wearable apparatus 200 may measure raw data corresponding to the EEG of the user by using the measurement electrode 271 and the reference electrode 272. The raw data corresponding to the measured EEG of the user may be stored in the storage unit 275 under control of the controller 210.

The controller 210 of the wearable apparatus 200 may convert the measured draw data into digital data. The converted digital data may be stored in the storage unit 275 under control of the controller 210.

The raw data may be stored as EEG information of the user, including an ID for a history management, a wearable apparatus name, the number of sensors, the number of electrodes, a measurement date, a measurement time, or raw data (or converted digital data), in the storage unit 275.

The controller 210 of the wearable apparatus 200 may transmit at least one selected from the raw data, the digital data, and EEG information of the user stored in the storage unit 275 to the portable apparatus 100 through the communicator 230. The controller 210 of the wearable apparatus 200 may also transmit the EEG information of the user stored in the storage unit 275 to the portable apparatus 100 through the communicator 230.

In various embodiments of the present disclosure, the EEG information of the user may include the raw data or the converted digital data.

The controller 210 of the wearable apparatus 200 may periodically (e.g., 100 msec that is changeable by setting) transmit the stored raw data and/or digital data to the portable apparatus 100 through the communicator 230.

The controller 110 of the portable apparatus 100 may receive the EEG information of the user from the wearable apparatus 200 through a communicator. The storage unit 175 may store the received EEG information of the user under control of the controller 110.

In operation S440 of FIG. 4, a content is displayed on a screen of the portable apparatus.

Figure 5C:
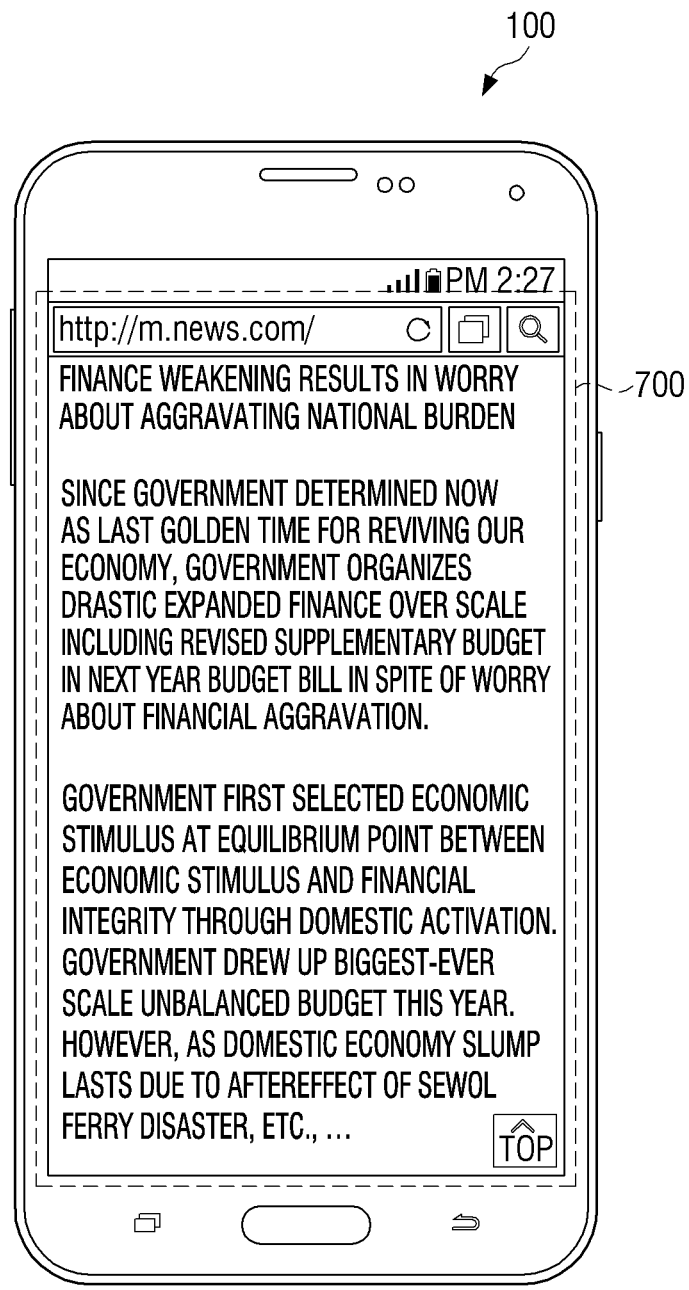

Referring to FIG. 5C, the controller 110 of the portable apparatus 100 may display a content (e.g., a webpage 700) on the screen. That is, the user may touch a shortcut icon 193d of FIG. 5A corresponding to a web browser.

The controller 110 may detect a touch (not shown) by using the touch screen 190 and the touch screen controller 195. The controller 110 may calculate a touch location (e.g., X and Y coordinates (not shown)) corresponding to the touch by using an electrical signal received from the touch screen controller 195.

A detection of a touch on a shortcut icon corresponding to a web browser performed in operation S440 of FIG. 4 is similar to the detection of the first touch performed in operation S410 of FIG. 4, and thus a repeated description thereof is omitted.

Referring to FIG. 5C, the controller 110 may execute a web browser in response to the touch. The controller 110 may display the webpage 700 through the web browser executed in response to the touch. The user may perform web surfing by using the displayed web browser.

It will be easily understood by those skilled in the art that a web browser displaying a content (e.g., a webpage) is one of various embodiments of the present disclosure, and various types of applications displaying (or playing) various types of contents including a video player playing an audio file or a video file, a music player playing a music file, a photo gallery displaying a photo file, a word processor writing a document, etc. may be executed by an input of a user.

In operation S450 of FIG. 4, EEG information is received from the wearable apparatus.

Figure 5D:
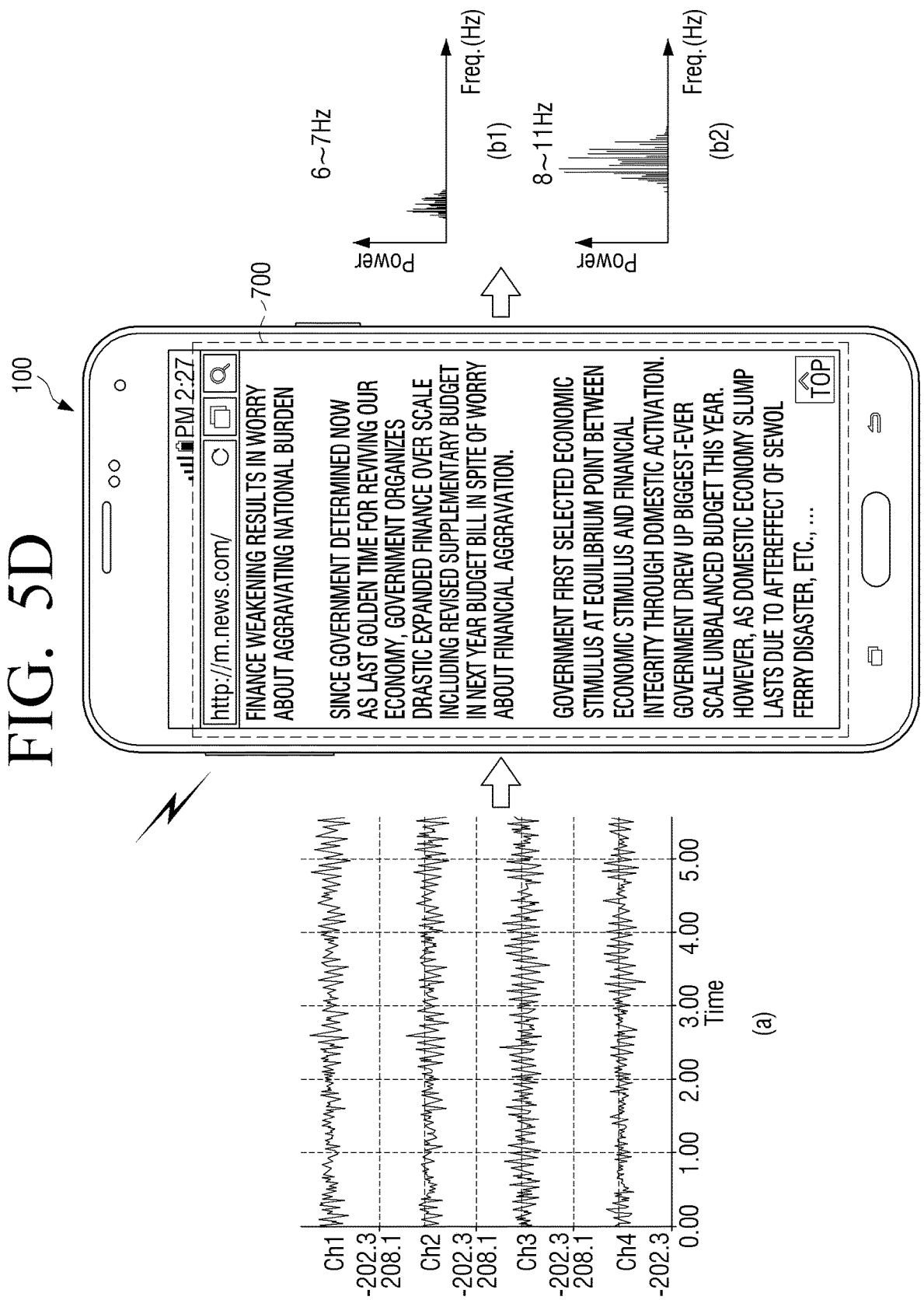

Referring to FIG. 5D, the controller 110 of the portable apparatus 100 may receive EEG information of the user from the wearable apparatus 200 through a communicator. The received EEG information of the user may include raw data or converted digital data.

The EEG information of the user received from the wearable apparatus 200 may vary in response to the number of the measurement electrodes 271 of the wearable apparatus 200. If the number of measurement electrodes 271 of the wearable apparatus 200 is 2 (e.g., refer to FIG. 3A), the received EEG information of the user may correspond to 2 channels. If the number of measurement electrodes 271 of the wearable apparatus 200 is 3 (e.g., refer to FIG. 3B), the received EEG information of the user may correspond to 2 channels. In (a) of FIG. 5D, the EEG information of the user received from the wearable apparatus 200 may correspond to 4 channels.

The storage unit 175 may store the received EEG information of the user under control of the controller 110.

The controller 110 may first calculate a visual fatigue of the user who is in a rest status, by using the wearable apparatus 200.

A generation equation for calculating the visual fatigue of the user may be expressed as in Equation 1 below. The controller 110 may perform an operation by using Equation 1 below to calculate the visual fatigue of the user.

$$\text{Visual Fatigue} = \frac{(\theta + \alpha)}{\beta} \quad \text{Equation 1}$$

In Equation 1 above, θ denotes a size of a theta wave, α denotes a size of an alpha wave, and β denotes a size of a beta wave. The visual fatigue calculated by using Equation 1 above may have a range between 01 and 3.4. The visual fatigue in the rest status may be lower than or equal to 2.2. Also, if the visual fatigue is higher than or equal to 2.6, the controller 110 may determine an increase in the visual fatigue.

The controller 110 may determine a visual fatigue of the user in the rest status by using received user EEG and Equation 1. The controller 110 may also determine the visual fatigue of the user in the rest status by using user EEG received in a pre-stored user visual fatigue range (e.g., calculated by using Equation 1). For example, the user visual fatigue in the rest status may be lower than or equal to about 2.2. A threshold value corresponding to an increase in a visual fatigue may be 2.6. The threshold value may be changed by a body condition and/or a surrounding environment of the user.

The calculated user visual fatigue in the rest status may be stored in the storage unit 175 under control of the controller 110.

It will be easily understood by those skilled in the art that the calculated user visual fatigue in the rest status may be changed by the body condition and/or the surrounding environment of the user.

The controller 110 may determine the increase in the visual fatigue of the user by using a pre-stored user visual fatigue in a rest status.

In operation S460 of FIG. 4, the received EEG information of the user is analyzed.

Referring to FIG. 5D, the controller 110 may calculate the visual fatigue of the user by using the received EEG information of the user and a visual fatigue application. The controller 110 may analyze user EEG according to frequency bands by using the visual fatigue application. The controller 110 may perform fast fourier transform (FFT) on the received EEG information of the user to analyze the received EEG information of the user. For example, if an amplitude change is large on a horizontal axis (e.g., time) of (a) of FIG. 5D, a frequency component may be located in a high area of a vertical axis (e.g., power) of (b) of FIG. 5D.

The controller 110 may calculate the visual fatigue by using a difference in a latency of a peak value of two EEGs that are respectively measured by a measurement electrode 271 located in an occipital lobe accepting a visual stimulus from the received EEG information of the user and a measurement electrode 271 located in a frontal lobe processing the visual stimulus. The latency may refer to a time when waves of EEG greatly fluctuate after receiving a stimulus with an increase in the visual fatigue of the user. The controller 110 may generate an average frequency component of EEG for a total period for which user EEG is collected through FFT.

The calculated visual fatigue may be stored in the storage unit 175 under control of the controller 110.

In operation S470 of FIG. 4, it is determined whether the visual fatigue increases.

As in (b1) and (b2) of FIG. 5D, the controller 110 may determine an increase in the visual fatigue. If the visual fatigue of the user increases, power of θ and a wave bands may increase. If power increases in a band between 6 Hz and 7 Hz, which is a θ wave, through an analysis of user EEG, the controller 110 may determine an occurrence of a visual fatigue of the user. Also, if power increases in a band between 8 Hz and 11 Hz, which is an a wave through a user EEG analysis, the controller 110 may determine an occurrence in the visual fatigue of the user.

The controller 110 may compare a pre-stored visual fatigue in a rest status and a visual fatigue calculated from the received EEG information of the user. If the visual fatigue calculated by using the received EEG information of the user and Equation 1 is higher than or equal to 2.6, the controller 110 may determine the increase in the visual fatigue of the user.

The controller 110 may determine the increase in the visual fatigue of the user by using one or both of a power increase of the 0 wave band and a power increase of the α wave band.

If it is determined in operation S470 of FIG. 4 that the visual fatigue does not occur, the method of changing the content screen of the portable apparatus ends.

On the other hand, if it is determined in operation S470 that the visual fatigue does occur, a displayed content is changed in operation S480.

Referring to FIGS. 5E to 11B, the controller 110 may change a content (e.g., a webpage) displayed on a web browser.

Figure 5E:
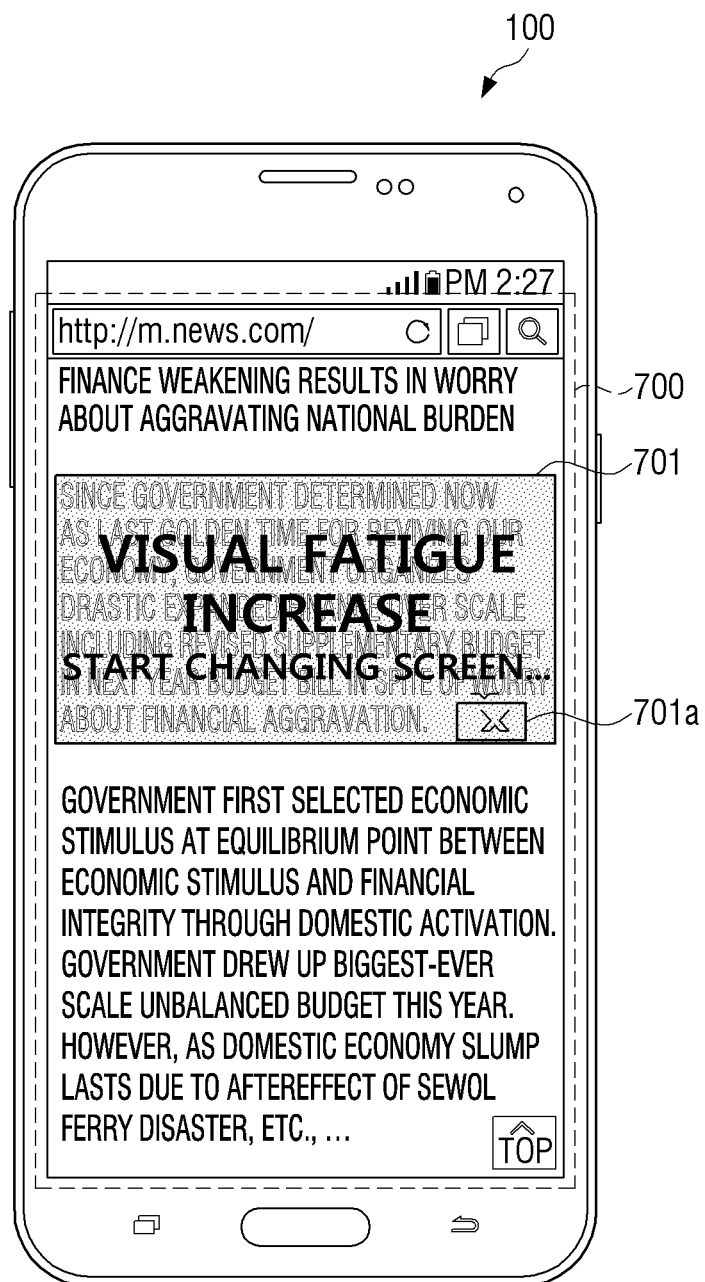

Referring to FIG. 5E, the controller 110 may display a pop-up window 701 corresponding to an occurrence of a visual fatigue of the user. The controller 110 may display the pop-up window 701 to distinguish the pop-up window 701 from the webpage 700. The controller 110 may display the pop-up window 701 having a transparency (e.g., a value between 0% and 100%). The transparency may be changed through an environment setting.

The controller 110 may display the pop-up window 701 so as to overlap the pop-up window 701 with the webpage 700. The controller 110 may display the pop-up window 701 for a determined time (e.g., 1 sec that is changeable by an environment setting).

A size of the displayed pop-up window 701 is smaller than a size of the webpage 700. For example, the size of the pop-up window 701 may include a range between 10% and 85% based on the size of the webpage 700. Also, the size of the pop-up window 701 may include a range between 30% and 55% based on the size of the webpage 700.

If an icon 701*a* is selected, the controller 100 may enable the displayed pop-up window 701 to disappear.

Also, the controller 110 may change the content 700 displayed on the web browser into another content 710 without displaying the pop-up window 701. The controller 110 may quickly (e.g., in response to a display time of the pop-up window 701) change the content 700 displayed on the web browser into the other content 710 without displaying the pop-up window 701.

If a preset time elapses or the icon 701*a* is selected, the controller 110 may change the displayed webpage 700. If the preset time elapses or the icon 701*a* is selected, the controller 110 may change the displayed webpage 700 by using an environment setting (e.g., a visual fatigue environment setting as shown in FIGS. 12A to 12C). If the preset time elapses or the icon 701*a* is selected, the controller 110 may change the displayed webpage 700 by using an environment setting (e.g., a visual fatigue environment setting as shown in FIGS. 12A to 12C) and portable apparatus information (e.g., a resolution, a screen size, or the like).

Figure 5F:

Referring to FIG. 5F, the controller 110 may change the webpage 700 into the other webpage 710 having a changed font size in response to the increase in the visual fatigue of the user. A font size of the changed webpage 710 may be larger than a font size of the original webpage 700. For example, if the font size of the original webpage 700 is 20 pixels, the font size of the changed webpage 710 may be 40 pixels (e.g., may be two times larger than the font size of the original webpage 700). A font size may include a scale-independent pixel (sp) or a device-independent pixel (dp).

It will be easily understood by those skilled in the art that a two-times increase in the font size of the changed webpage 710 is one embodiment, and the font size of the changed webpage 710 may be changed into other various types of font sizes.

The font size may be changed in response to an application executed in the portable apparatus 100. If the visual fatigue of the user occurs, the controller 110 may differently change the font size in response to the application executed in the portable apparatus 100. For example, if the visual fatigue of the user occurs, the controller 110 may differently change a font size of a webpage displayed on a web browser and a font size of a text displayed on a processor.

As shown in FIG. 5F, the visual fatigue of the user may decrease by the webpage 710 having a changed font size.

If the content is changed into another content, the controller 110 may continuously calculate the visual fatigue by using the received EEG information of the user.

If the calculated visual fatigue of the user decreases, the controller 110 may restore the displayed other content 710 to the content 700 that is unchanged.

It will be easily understood by those skilled in the art that different font sizes displayed on a web browser and a word processor are one embodiment and may be changed in response to various types of applications. Also, it will be easily understood by those skilled in the art that the font size may be changed in response to the increase in the visual fatigue of the user so as to correspond to a screen size and/or a resolution of the portable apparatus 100.

Figure 6A:
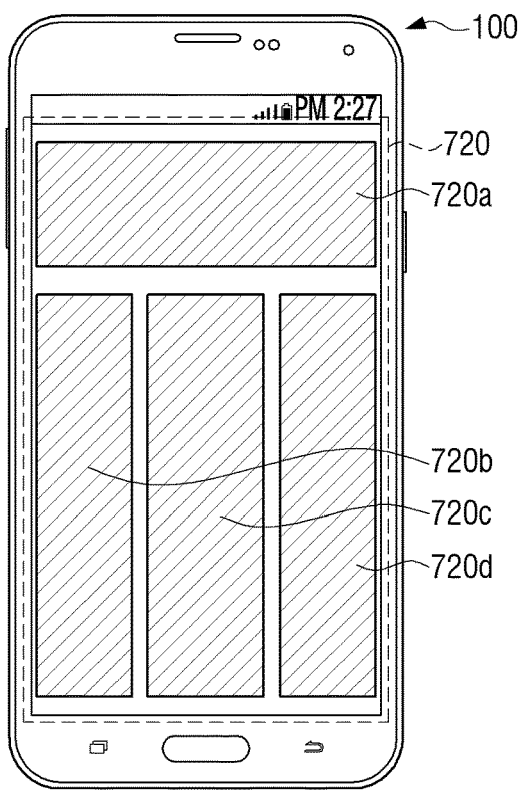
Figure 6B:
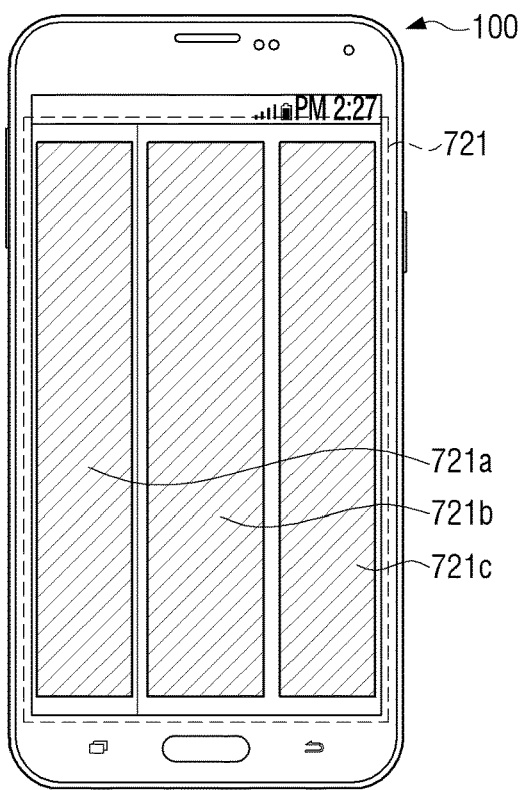
Figure 6C:
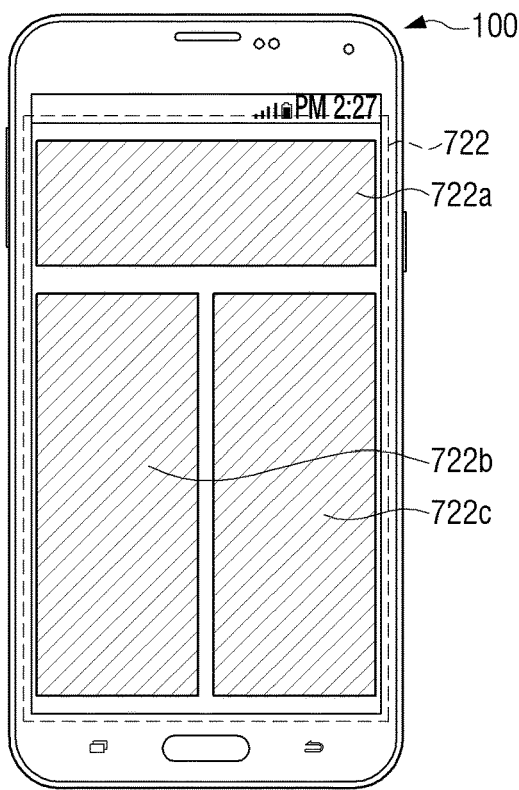
Figure 6D:
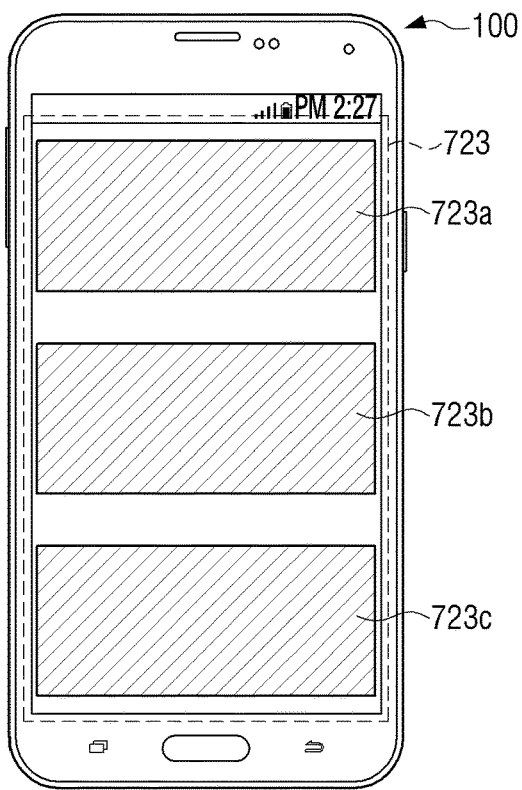

Referring to FIGS. 6A to 6D, the controller 110 may change the webpage 700 into a webpage 720 having a changed layout in response to an increase in a visual fatigue of the user. The changed layout of the webpage 720 may be a layout where the original webpage 700 is divided into three areas (e.g., as shown in FIGS. 6B, 6C, and 6D) or four areas (e.g., as shown in FIG. 6A). The changed layout of the webpage 720 may be divided into two areas (not shown) or five or more areas. A text, an image, or a moving image (e.g., a flash or the like) included in the webpage 700 may be displayed in the changed layout of the webpage 720.

As shown in FIG. 6A, the changed layout of the webpage 720 may include one horizontal area 720*a* and three vertical areas 720*b*, 720*c*, and 720*d*. Widths of spaces between the areas 720*a* through 720*d* may be smaller than one of a height and a width of each of the areas 720*a* through 720*d*. Also, areas of the three vertical areas 720*b* through 720*d* may be different from one another.

As shown in FIG. 6B, the changed layout of a webpage 721 may include three vertical areas 721*a*, 721*b*, and 721*c*. Widths of spaces between the areas 721*a* through 721*c* may be smaller than one of widths of the three areas 721*a* through 721*c*. Areas of the three vertical areas 721*a* through 721*c* may be different from one another. Areas of two of the three vertical areas 721*a* through 721*c* may be the same.

As shown in FIG. 6C, a changed layout of a webpage 722 may include one horizontal area 722*a* and two vertical areas 722*b* and 722*c*. Widths of spaces between the areas 722*a* through 722*c* may be smaller than one of a height and a width of each of the areas 722*a* through 722*c*. Areas of the two vertical areas 722*b* and 722*c* may be different from each other. Also, areas of two of the three areas 722*a* through 722*c* may be the same.

As shown in FIG. 6D, a changed layout of a webpage 723 may include three horizontal areas 723*a*, 723*b*, and 723*c*. Widths of spaces between the three horizontal areas 723*a* through 723*c* may be smaller than one of widths of the three horizontal areas 723*a* through 723*c*. Areas of the three horizontal areas 723*a* through 723*c* may be different from one another. Areas of two of the three horizontal areas 723*a* through 723*c* may be the same.

A visual fatigue of a user may decrease by a change in an ocular movement direction and/or a changing of a focus direction caused by the changed layout of the webpage 720 as shown in FIGS. 6A to 6D.

If a content is changed into another content, the controller 110 may continuously calculate the visual fatigue by using the received EEG information of the user.

If the calculated visual fatigue of the user decreases, the controller 110 may restore the displayed other contents 720 through 723 to the content 700.

It will be easily understood by those skilled in the art that layouts as shown in FIGS. 6A to 6D are embodiments, and thus layouts, areas included in the layouts, and locations of the areas included in the layouts may be changed in response to various types of applications.

Figure 7A:
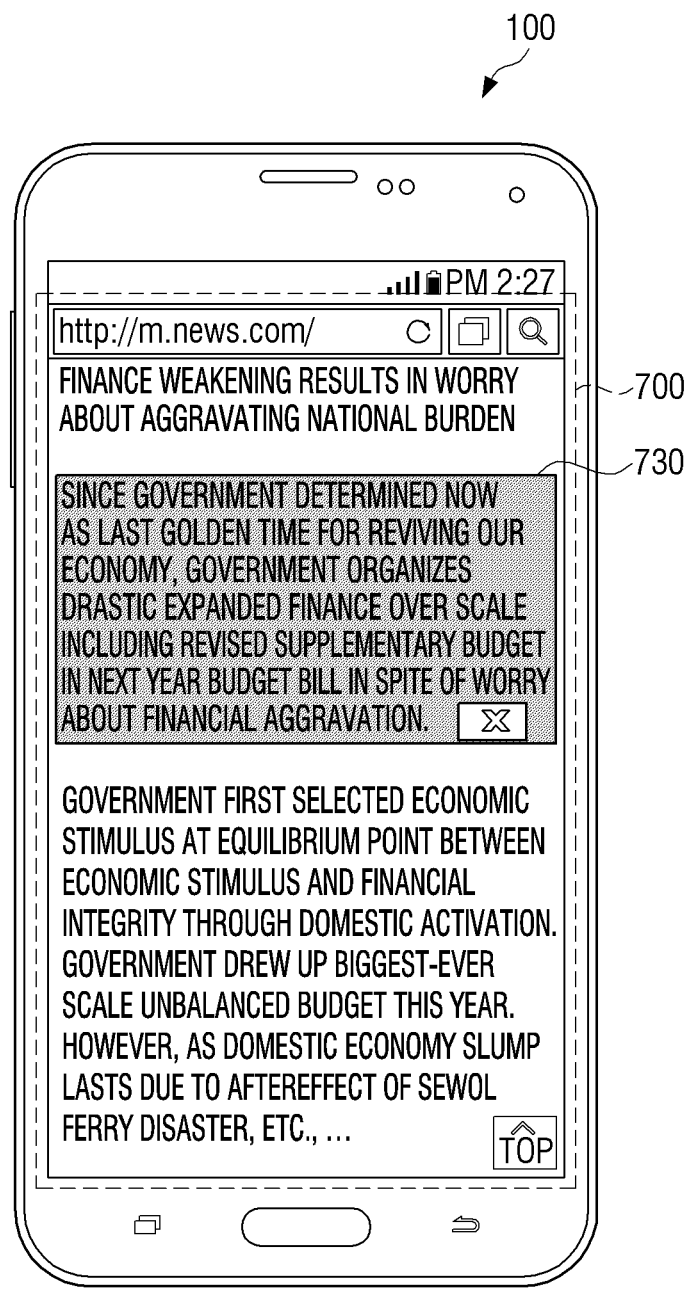
Figure 7B:
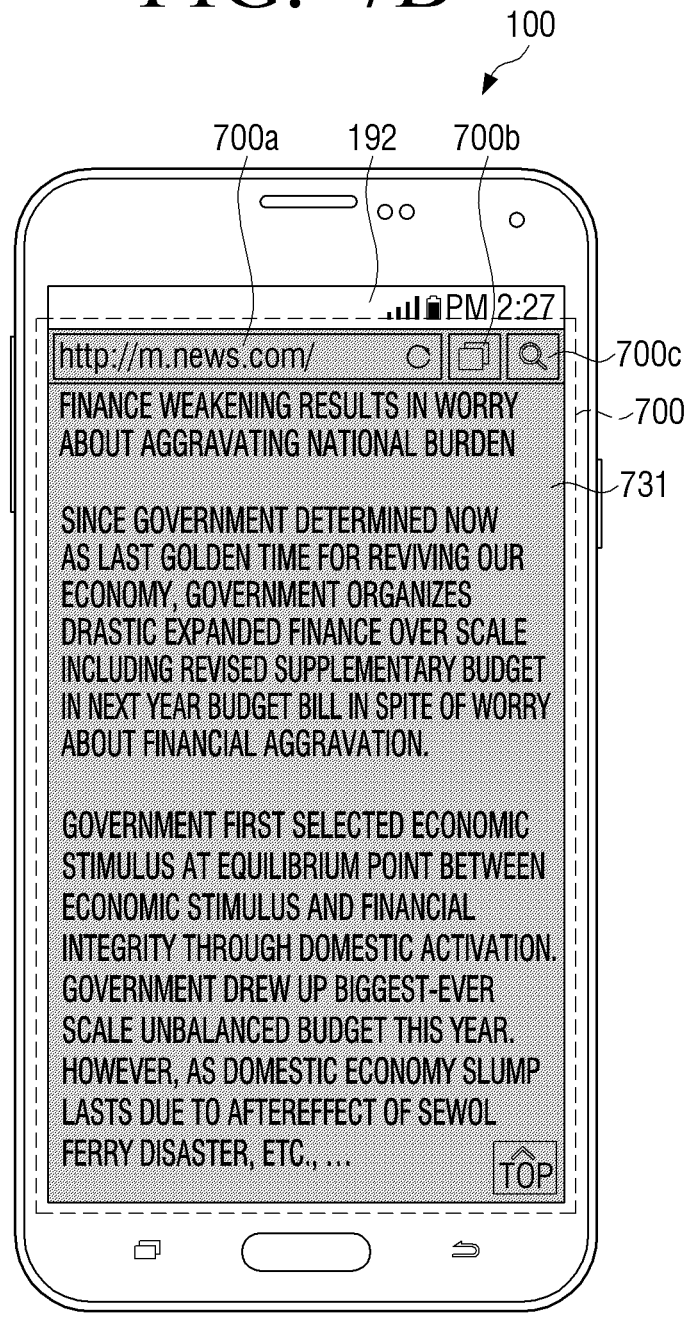

Referring to FIGS. 7A and 7B, the controller 110 may change (or add) a webpage 700 to a webpage including a color screen 730 or 731 in response to an increase in a visual fatigue of a user. The color screen 730 or 731 may include a green area or a greenish area (e.g., a yellowish green area, a dark green area, or the like) that does not give a great stimulus to eyes of the user. The color screen 730 or 731 may be alternatively be considered a "color filter".

The controller 110 may display the color screen 730 or 731 in an area set on the webpage 700. The controller 110 may add the color screen 730 or 731 so as to overlap the color screen 730 or 731 with the webpage 700. The color screen 730 or 731 may have a transparency (e.g., a value between 0% and 100% that is changeable by an environment setting).

An area of the color screen 730 may be between 30% and 50% of an area of the webpage 700. An area of the color screen 731 may be the same as the area of the webpage 700. The area of the color screen 731 may be an area except at least one selected from an address display bar 700*a*, a tap icon 700*b*, and a search icon 700*c* on the webpage 700. The area of the color screen 731 may also include a status bar 192 and the webpage 700.

The displayed color screen 730 may include a polygonal, circular, or freestyle shape. The color screen 730 may be located in one of an upper area, a central area, and a lower area based on a central area of the webpage 700.

Color screen information (e.g., an ID for a history management, a color of a color screen, a size of the color screen, a storage location of the color screen, a location of the color screen in a webpage, or the like) corresponding to the color screen 730 or 731 may be stored in the storage unit 175 under control of the controller 110.

The controller 110 may change a background color of the webpage 700 into one of a green color and a greenish color so as to enable the background color of the webpage 700 to correspond to the color screen 730 or 731.

Figure 7C:
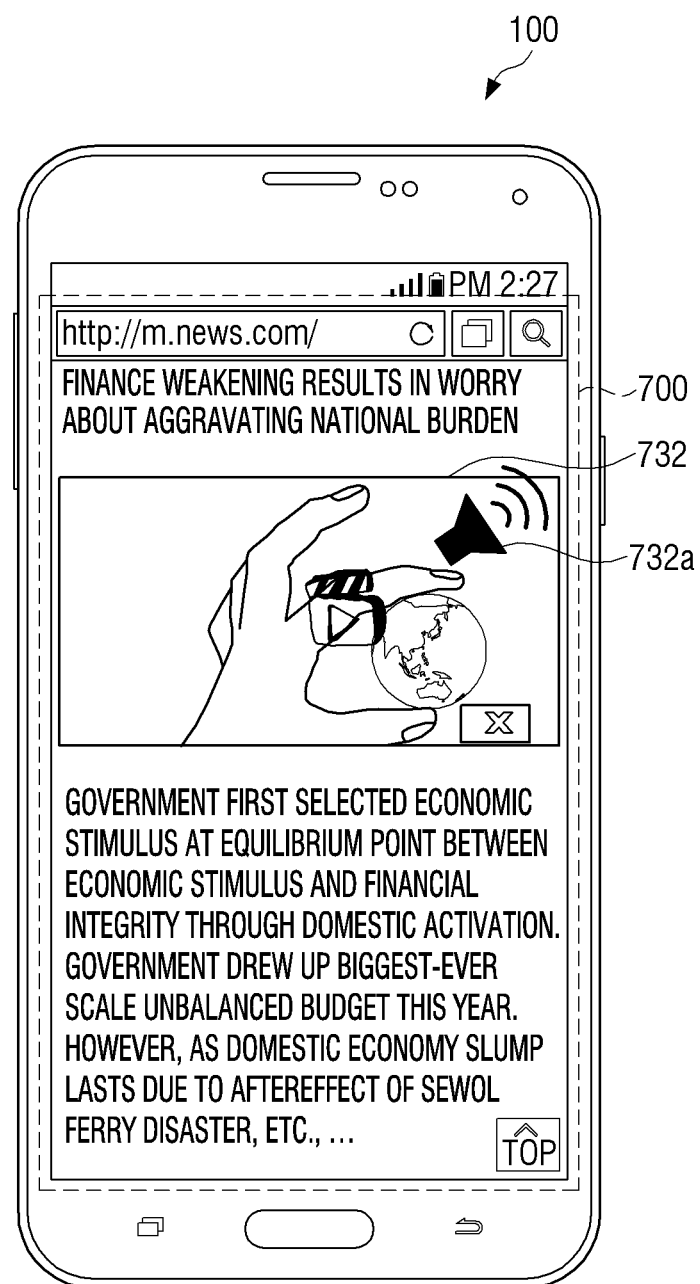

Referring to FIG. 7C, the controller 110 may change the webpage 700 into a webpage 700 including a visual fatigue relax video 732 in response to the increase in the visual fatigue of the user.

The visual fatigue relax video 732 may be a visual fatigue relax video (e.g., a forest landscape or the like) of a green color or a greenish color (e.g., a yellowish green color, a dark green color or the like) that does not give a great stimulus to the eyes of the user.

The controller 110 may display the visual fatigue relax video 732 so as to overlap with the webpage 700. The visual fatigue relax video 732 may have a transparency (e.g., a value between 0% and 100% that is changeable by an environment setting).

An area of the visual fatigue relax video 732 may be between 25% and 85% of an area of the webpage 700. The area of the visual fatigue relax video 732 may also be the same as the area of the webpage 700. The visual fatigue relax video 732 may be located in one of an upper area, a central area, and a lower area based on a central area of the webpage 700.

Visual fatigue relax video information (e.g., an ID for a history management, a visual fatigue relax video name, a visual fatigue relax video play time, a visual fatigue relax video storage location, a location of a visual fatigue relax video in a webpage, or the like) corresponding to the visual fatigue relax video 732 may be stored in the storage unit 175 under control of the controller 110.

The visual fatigue relax video 732 may include a text to speech (TTS) service. The controller 110 may convert a text included in the webpage 700 into a voice and output the voice in response to the increase in the visual fatigue of the user. If the text is converted into the voice and then output, the controller 110 may display a speaker icon 732*a*.

If the content is changed into another content, the controller 110 may continuously calculate the visual fatigue by using received EEG information of the user.

If the calculated visual fatigue of the user decreases, the controller 110 may restore displayed other contents 730 through 732 to the content 700 that is unchanged.

Figure 8A:
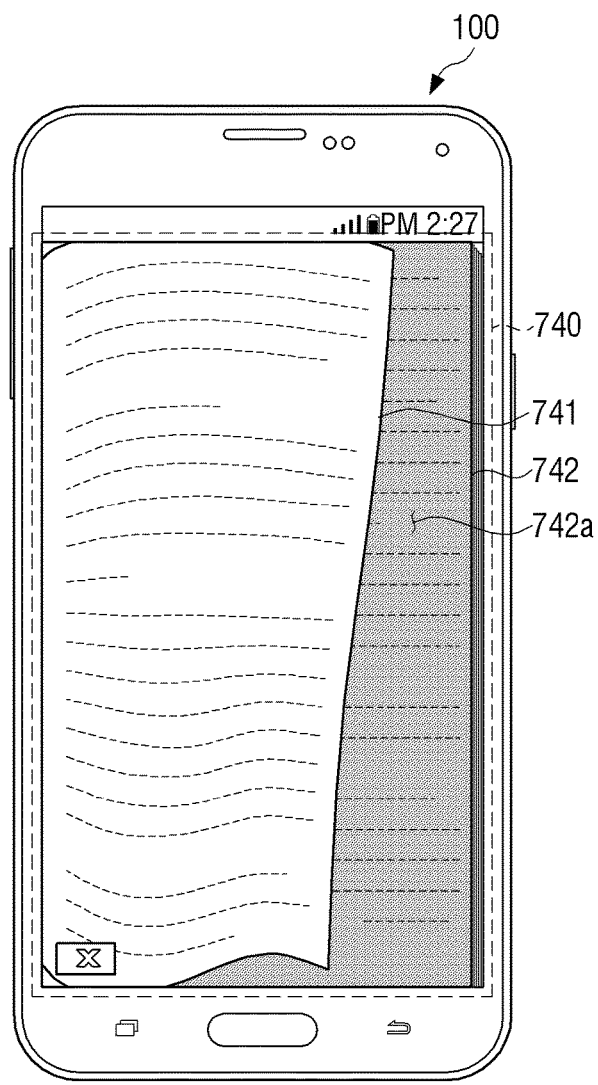
Figure 8B:
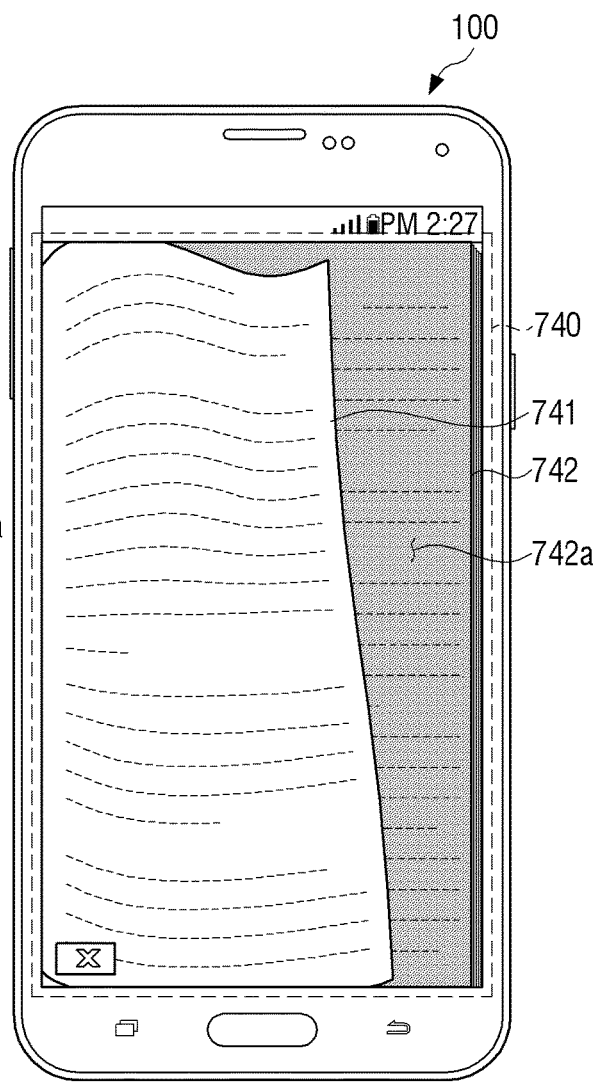

Referring to FIGS. 8A and 8B, a first e-book screen 740 may be displayed on a screen of the portable apparatus 100. If a current page 741 goes to the left by the user on the first e-book screen 740, the controller 110 may display a visual fatigue relax color screen 742*a* on a next page 742 of the first e-book screen 740 in response to an increase in a visual fatigue of a user.

If the current page 741 is modified into a convex shape and then goes to the left through a user input, the controller 110 may display the visual fatigue relax color screen 742*a* so as to overlap the visual fatigue relax color screen 742*a* with the next page 742. The visual fatigue relax color screen 742*a* may have a transparency (e.g., a value between 0% and 100% that is changeable by an environment setting).

If the current page 741 is modified into the convex shape and then goes to the left in response to a location of the user input (e.g., a touch or a touch gesture) (e.g., as shown in FIGS. 8A and 8B), the controller 110 may differently display the visual fatigue relax color screen 742*a* displayed on the next page 742.

If the current page 741 is upwards modified into a convex shape through a user input and then gradually goes to the left, the controller 110 may display a larger part of the visual fatigue relax color screen 742*a* on the next page 742.

The controller 110 may change a background color of the next page 742 into one of a green color and a greenish color in response to the visual fatigue relax color screen 742*a*.

If the content is changed into another content, the controller 110 may continuously calculate the visual fatigue by using received EEG information of the user.

If the calculated visual fatigue of the user decreases, the controller 110 may restore the content 742 to the content 741.

Figure 9A:
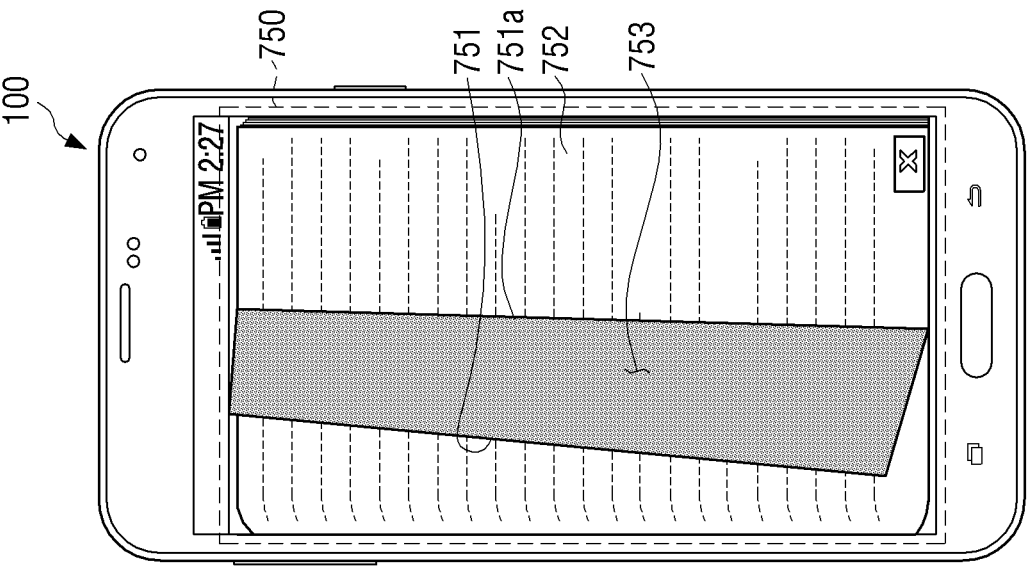
Figure 9B:
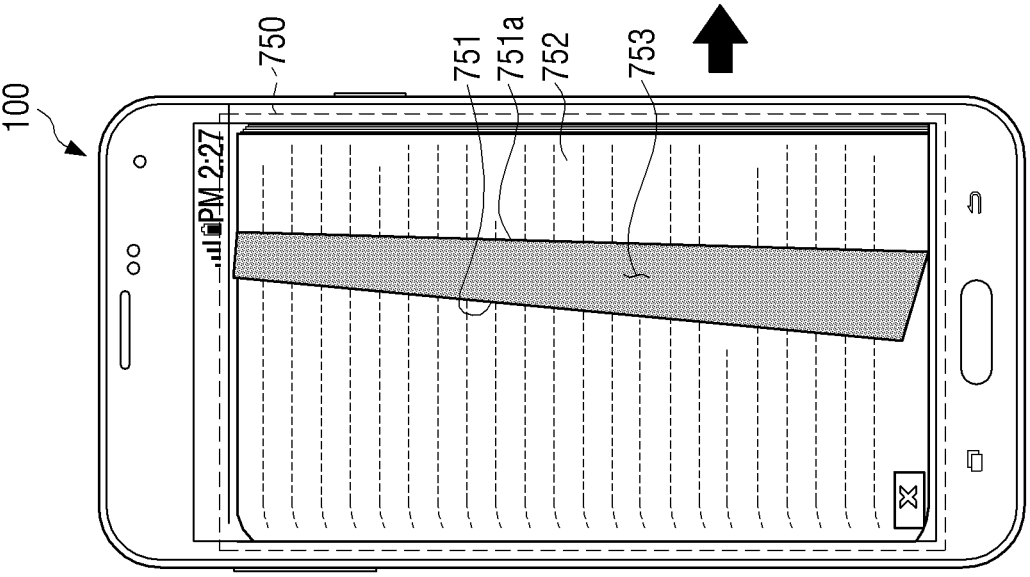
Figure 9C:
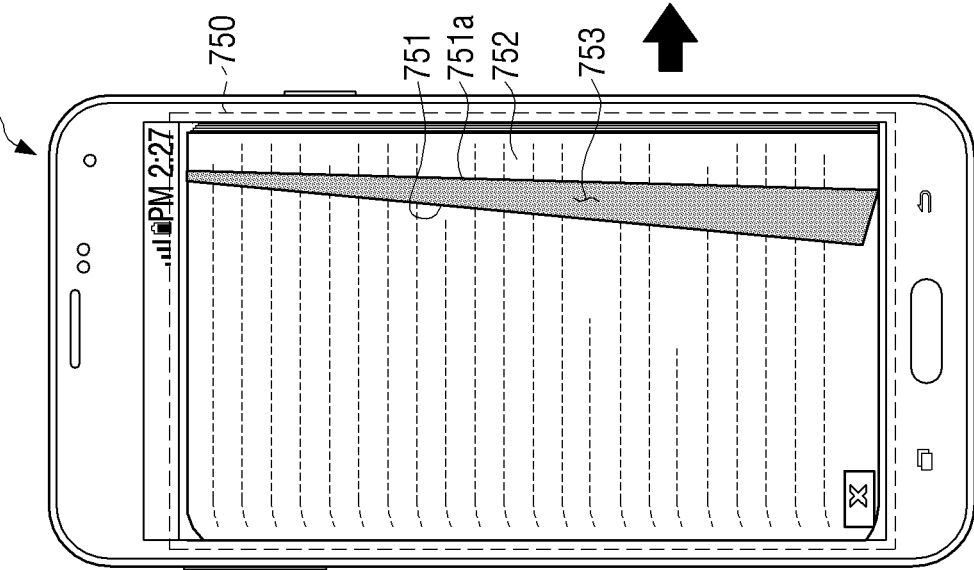

Referring to FIGS. 9A to 9C, a second e-book screen 750 may be displayed on a screen of the portable apparatus 100. If a current page 751 goes to the left on the second e-book screen 750 by a user, the controller 110 may display a visual fatigue relax color screen 753 on a back surface 751*a* of the current page 751 on the second e-book screen 750 in response to an increase in a visual fatigue of the user. A next page 752 does not overlap with the visual fatigue relax color screen 753.

If the current page 751 is folded and then goes to the left through a user input, the controller 110 may display the visual fatigue relax color screen 753 so as to overlap the visual fatigue relax color screen 753 with the back surface 751*a* of the current page 751. The visual fatigue relax color screen 753 may have a transparency (e.g., a value between 0% and 100% that is changeable by an environment setting).

If the current page 751 is folded and then goes to the left (as shown in FIGS. 9A to 9C) in response to a location of the user input (e.g., a touch or a touch gesture), the controller 110 may differently display the back surface 751*a* of the current page 751.

If the current page 751 is folded and then gradually goes to the left through a user input, the controller 110 may display a larger part of the visual fatigue relax color screen 753 on the back surface 751*a* of the current page 751.

If a content is changed into another content, the controller 110 may continuously calculate the visual fatigue by using received EEG information of the user.

If the calculated visual fatigue of the user decreases, the controller 110 may restore the content 753 to the content 751.

Figure 10A:
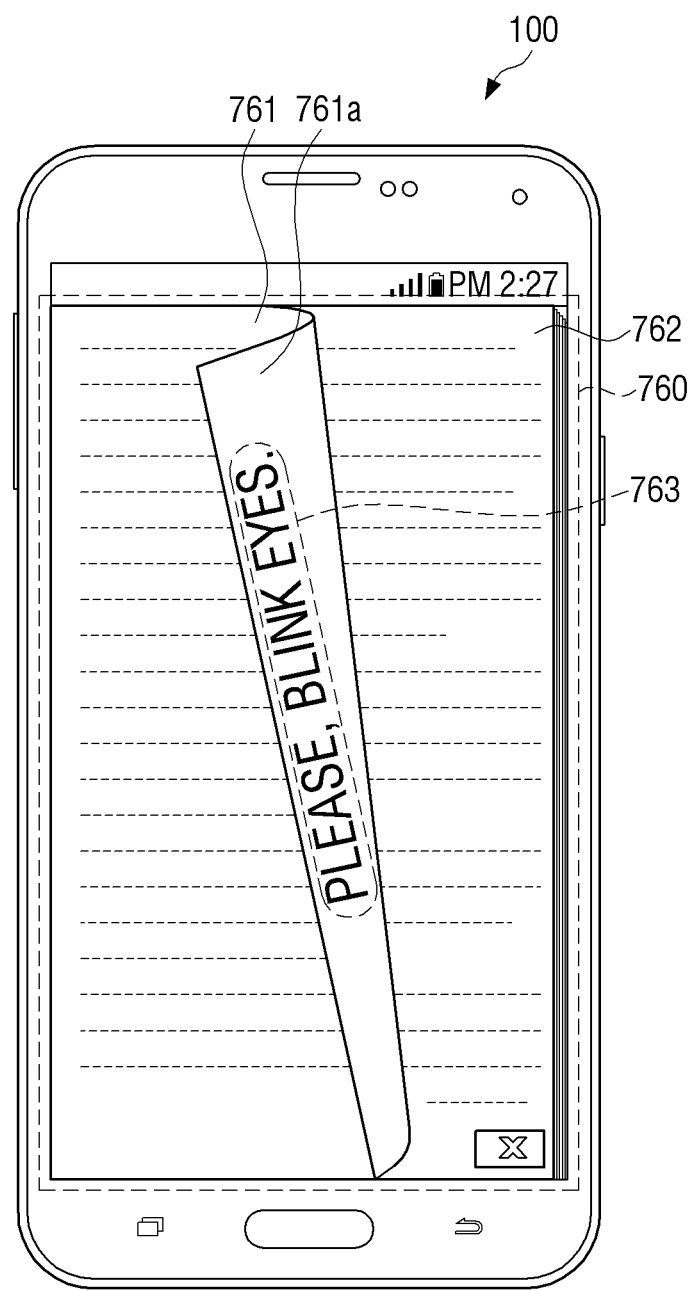

Referring to FIG. 10A, a third e-book screen 760 may be displayed on a screen of the portable apparatus 100. If a current page 761 goes to the left on the third e-book screen 760 by a user, the controller 110 may display an ocular movement guide 763 on a back surface 761*a* of the current page 761 on the third e-book screen 760 in response to an increase in a visual fatigue of the user. For example, the ocular movement guide 763 may include "Please, blink eyes.", "Please, move eyes up and down.", "Please, move eyes from side to side.", or "Please, move eyes up, down, and from side to side."

The ocular movement guide 763 displayed on the back surface 761a of the current page 761 may be realized as one of a text, an image, and a moving image. For example, if the ocular movement guide 763 is the text, a font size of the displayed content may correspond to an area of the back surface 761a. For example, as shown in FIG. 10A, if the area of the back surface 761a of the current 761 is 20% of the current page 761, the font size of the text may be 20 pixels in the ocular movement guide 763. If the current page 761 goes to the left more, and thus the area of the back surface 761a is 40% of the current page 761, the font size of the text may be 35 pixels in the ocular movement guide 763 in response to the increased area of the back surface 761a. As the area of the back surface 761a increases, the font size of the text may increase in the ocular movement guide 763.

The ocular movement guide 763 displayed on the back surface 761a of the current page 761 does not overlap with a next page 762.

If the current page 761 is folded and then goes to the left through a user input, the controller 110 may display the ocular movement guide 763 on the back surface 761a of the current page 761. Also, if the current page 761 is folded and then goes to the left through the user input, the controller 110 may display the ocular movement guide 763 so as to overlap the ocular movement guide 763 with the back surface 761a of the current page 761. If the ocular movement guide 763 overlaps with the back surface 761a of the current page 761, the ocular movement guide 763 may have a transparency (e.g., a value between 0% and 100% that is changeable by an environment setting).

As shown in FIG. 10A, if the third e-book screen 760 is displayed on the screen of the portable apparatus 100, the controller 110 may execute a first camera 151.

The controller 110 may detect whether an ocular movement of the user corresponding to the ocular movement guide 763 is performed, by using the first camera 151. The controller 110 may detect whether the ocular movement of the user is performed, by using the first camera 151 and a face recognition. If the user blinks their eyes corresponding to the ocular movement guide 763, the controller 110 may detect nictations of the user by using the first camera 151 and the face recognition. For example, if the displayed ocular movement guide 763 is "Please, blink eyes 10 times.", the controller 110 may count the number of nictations of the user by using the first camera 151 and the face recognition. If the number of nictations is lower than 10 times, the controller 110 may not turn the current page 761 but may keep the current page 761.

The ocular movement guide 763 that is displayed in response to an increased degree of a visual fatigue may be changed (e.g., the number of nictations may increase with an increase in the number of nictations).

In various embodiments of the present disclosure, an ocular movement guide may be an ocular movement animation. Also, the ocular movement animation may include first through third exercise animations 764 of FIG. 10B, 771 of FIG. 11A, and 775 of FIG. 11B. An animation may refer to a moving image.

If a content is changed into another content, the controller 110 may continuously calculate a visual fatigue by using received EEG information of the user.

If the calculated visual fatigue of the user decreases, the controller 110 may restore the displayed content 761b to the content 760.

Figure 10B:
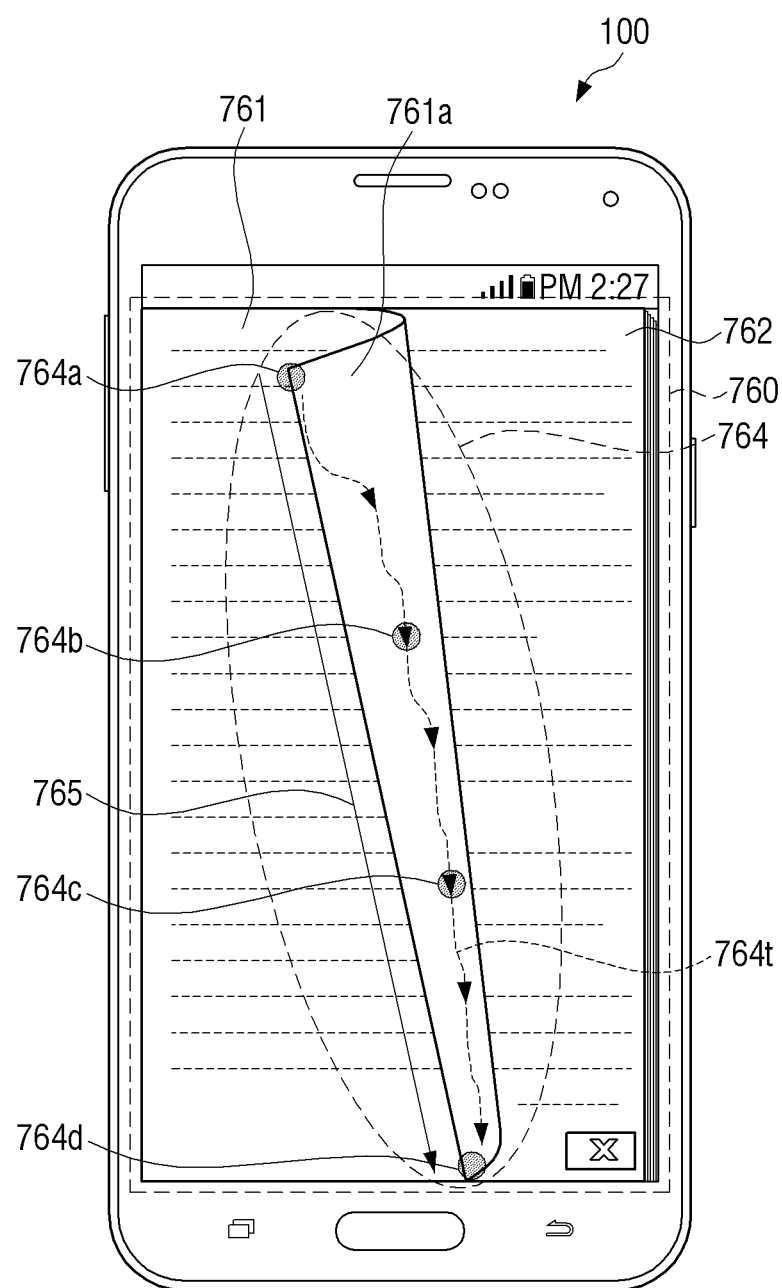

Referring to FIG. 10B, the third e-book screen 760 may be displayed on the screen of the portable apparatus 100. If the current page 761 goes to the left on the third e-book screen 760 by the user, the controller 110 may display the first ocular movement animation 764 on the back surface 761a of the current page 761 on the third e-book screen 760 in response to an increase in the visual fatigue of the user.

The first ocular movement animation 764 may be an animation corresponding to eye-tracking for tracking eyes of the user. For example, the controller 110 may detect user eyes located in a first point 764a that is an initial location in the first ocular movement animation 764 by using the first camera 151.

If the eyes of the user are detected from the first point 764a, the controller 110 may display a trajectory 764t inducing the eyes of the user downwards. Also, the controller 110 may further display a direction symbol 765 that is adjacent to the trajectory 764t and induces the eyes of the user downwards. The controller 110 may display the direction symbol 765 on the current page 761 or the next page 762.

The trajectory 764t may include intermediate points 764b and 764c from the first point 764a and a fourth point 764d that is a final location. The trajectory 764t includes a plurality of points, and four points 764a through 764d are only an example.

The controller 110 may detect the eyes of the user following the trajectory 764t by using the first camera 151 and eye-tracking. The controller 110 may detect the eyes of the user located in the fourth point 764d that is the final location in the first ocular movement animation 764, by using the first camera 151. If the eyes of the user are detected from the fourth point 764d, the controller 110 may repeat the first ocular movement animation 764.

If the number of times the eyes of the user follow the trajectory is lower than the number of times the first ocular movement animation 764 is repeated or the eyes of the user starting from the first point 764a are not detected from the fourth point 764d, the controller 110 may not turn the current page 761 but may keep the current page 761.

The first ocular movement animation 764 that is displayed in response to an increased degree of a visual fatigue may be changed (e.g., the trajectory 764t may be more curved with an increase in the visual fatigue).

If the content is changed into another content, the controller 110 may continuously calculate the visual fatigue by using received EEG information of the user.

If the calculated visual fatigue of the user decreases, the controller 110 may restore the displayed content 764 to the content 760.

Figure 11A:
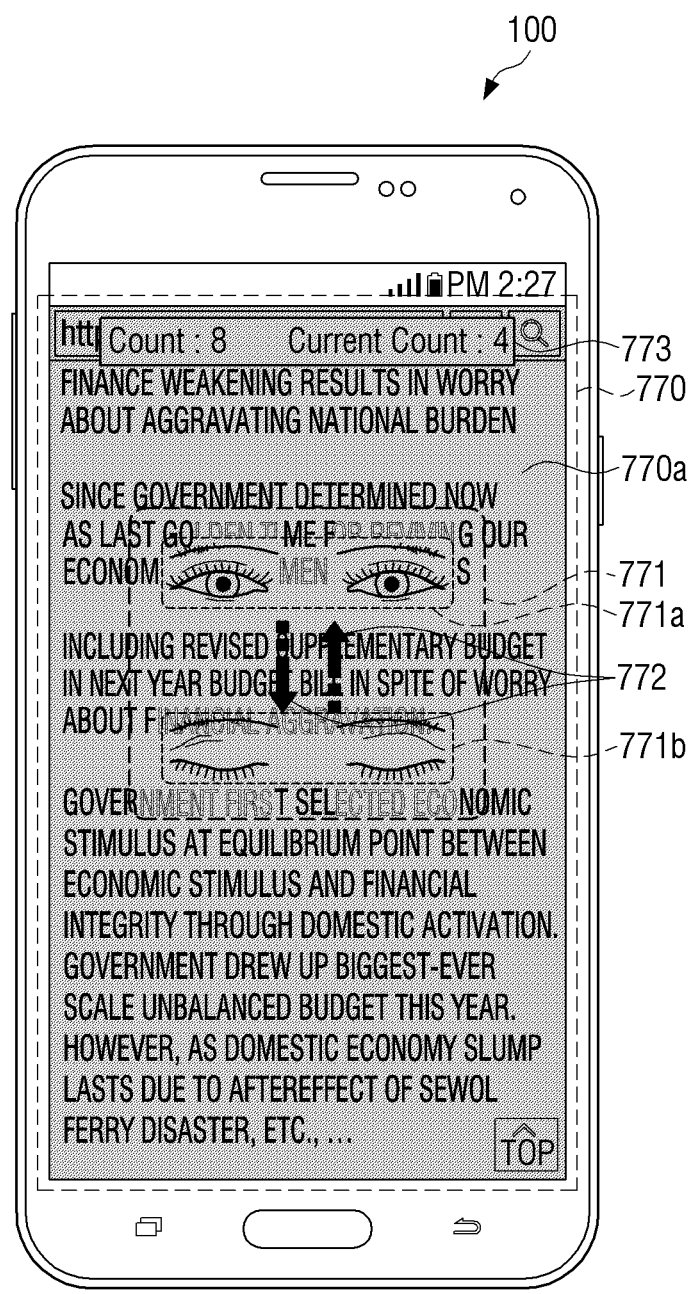

Referring to FIG. 11A, the controller 110 may change the webpage 700 into a webpage 770 including a color screen 770a in response to an increase in a visual fatigue of a user. The color screen 770a may include a green or greenish area (e.g., a yellowish green area, a dark green area, or the like) that does not give a great stimulus to eyes of the user.

The controller 110 may display a second ocular movement animation 771 so as to overlap the second ocular movement animation 771 with the color screen 770a of the webpage 770. The second ocular movement animation 771 may have a transparency (e.g., a value between 0% and 100% that is changeable by an environment setting).

The second ocular movement animation 771 may be an animation corresponding to an iris recognition for recognizing irises of the user. For example, the controller 110 may detect irises of the user located in a first location 771a, where eyes of the user are opened (e.g., the irises are recognized), from the second ocular movement animation 771 by using the first camera 151.

If the irises of the user are detected from the first location 771a, the controller 110 may display a direction symbol 772 that induces the eyes of the user downwards.

The controller 110 may detect nictations of the user corresponding to the direction symbol 772 by using the first camera 151 and the iris recognition. The controller 110 may detect eyelid closures of the user from a second location 771b that is a final location, in the second ocular movement animation 771 by using the first camera 151. If the eyelid closures are detected from the second location 771b, the controller 110 may repeat the second ocular movement animation 771.

The number of times the second ocular movement animation 771 being repeated may be displayed in a counter 773. The counter 773 may display the total number of repeated times and the current number of repeated times.

If the nictations of the user are lower than the total number of times the second ocular movement animation 764 is repeated, the controller 110 may not change the webpage 770 but may keep the webpage 770.

The second ocular movement animation 771 that is displayed in response to the increase in the visual fatigue may be changed (e.g., the number of repeated times the second ocular movement animation 771 being repeated may increase with the increase in the visual fatigue).

If a content is changed into another content, the controller 110 may continuously calculate the visual fatigue by using received EEG information of the user.

If the calculated visual fatigue of the user decreases, the controller 110 may restore the displayed contents 771, 772, and 773 to the content 770.

Figure 11B:
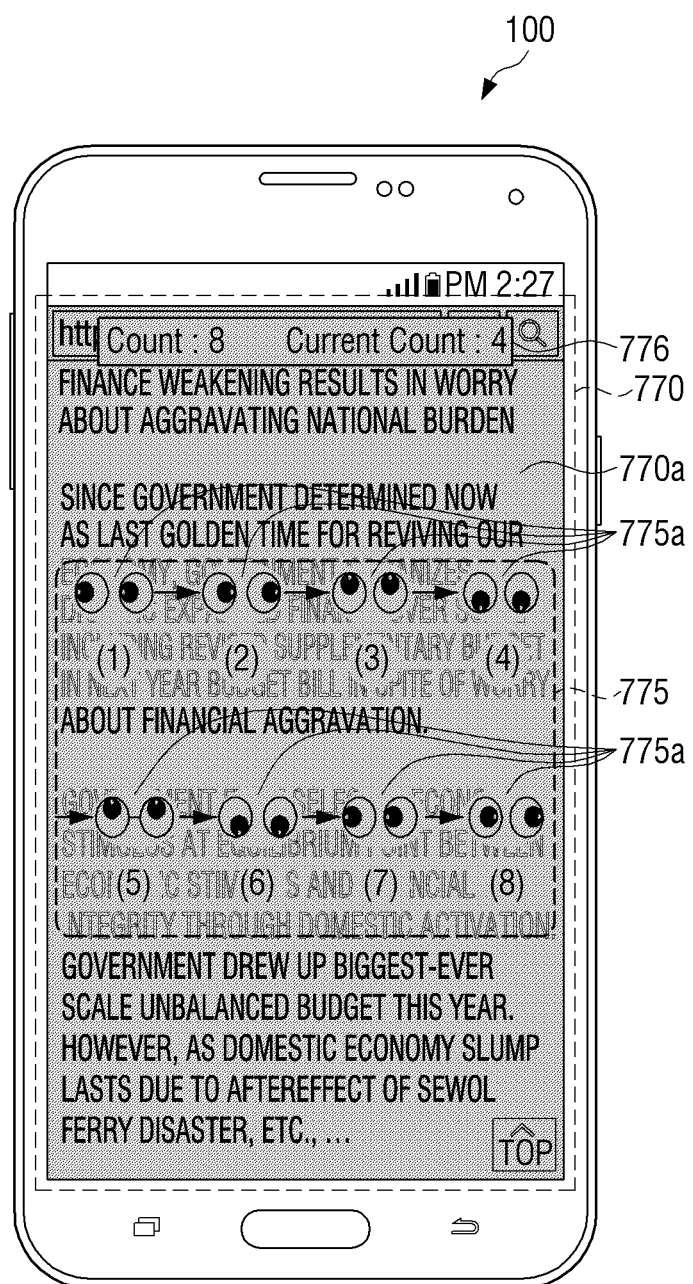

Referring to FIG. 11B, the controller 110 may change the webpage 700 into a webpage 770 including a color screen 770a in response to an increase in a visual fatigue of the user. The color screen 770a may include a green or greenish area (e.g., a yellowish green area, a dark green area, or the like) that does not give a great stimulus to the eyes of the user.

The controller 110 may display a third ocular movement animation 775 so as to overlap the third ocular movement animation 775 with the color screen 770a of the webpage 770. The third ocular movement animation 775 may have a transparency (e.g., a value between 0% and 100% that is changeable by an environment setting).

The third ocular movement animation 771 may be an animation corresponding to eye-tracking for tracking the eyes of the user. For example, the controller 110 may detect irises of the user corresponding to status 1, where both eyes of the user are moved to the left, from the third ocular movement animation 775.

If the irises of the user are detected in the status 1 where the both eyes of the user are moved to the left, the controller 110 may display a direction symbol 775a that induces the eyes of the user to the right.

The controller 110 may detect ocular movements of the user corresponding to the direction symbol 775a by using the first camera 151 and the iris recognition. The controller 110 may detect the irises of the user in a status 8, in which both eyes of the user are moved to the left and which is a final location, from the third ocular movement animation 771 by using the first camera 151. If the irises of the user are detected from the final location 8, the controller 110 may repeat the third ocular movement animation 775.

The number of times the third ocular movement animation 771 being repeated may be displayed in a counter 776. The counter 776 may display the total number of repeated times and the current number of repeated times.

If the total number of repeated times or the current number of repeated times is lower than the total number of the third ocular movement animation 775 being repeated, the controller 110 may not change the webpage 770 but may keep the webpage 770.

The third ocular movement animation 771 that is displayed in response to an increased degree of the visual fatigue may be changed (e.g., the number of repeated times the third ocular movement animation 771 being repeated may increase with the increase in the visual fatigue).

If the content is changed into another content, the controller 110 may continuously calculate the visual fatigue by using received EEG information of the user.

If the calculated visual fatigue of the user decreases, the controller 110 may restore the other contents 775 and 776 to the content 770.

If the displayed content is changed in operation S480 of FIG. 4, the method of changing the content screen of the portable apparatus ends.

In various embodiments of the present disclosure, the portable apparatus 100 may infer a visual fatigue without bio-information of the user (e.g., EEG information).

The controller 110 of the portable apparatus 100 may store a visual fatigue DB in the storage unit 175, wherein the visual fatigue DB corresponds to a visual fatigue calculated based on the bio-information of the user (e.g., EEG information) received from the wearable apparatus 200. The controller 110 of the portable apparatus 100 may infer a visual fatigue occurrence start time by using the stored visual fatigue DB without the bio-information of the user received from the wearable apparatus 200.

Visual fatigue items included in the visual fatigue DB may include an ID for a history management, an application type (e.g., a web browser, a video player, a game, or the like) executed in the portable apparatus 100, a content type (e.g., a webpage, a video, a game, or the like), an application execution start time, a visual fatigue occurrence time, a visual fatigue duration time, a visual fatigue occurrence cycle, user fatigue bio-information (e.g. a heart rate, a temperature, or the like if a visual fatigue occurs), another content change information (e.g., another content type, another content change start time, or the like), etc.

The controller 110 may manage a visual fatigue history of the user by using the accumulated visual fatigue DB. The controller 110 may learn the visual fatigue of the user by using the stored visual fatigue DB and machine learning. The controller 110 may learn the visual fatigue of the user by using the stored visual fatigue DB, a statistical analysis, a big data analysis, or machine learning. The statistical analysis may refer to a regression analysis, a time-series analysis, or an analysis using an execution of a regular check or the like in statistical software. Also, a computing apparatus may extract (or search for), analyze, and determine a pattern of accumulated big data, and infer a result through machine learning. The controller 110 may infer a visual fatigue through an accumulation of visual fatigue learning. The controller 110 may infer a visual fatigue of the user by using a stored visual fatigue DB, a statistical analysis, a big data analysis, or machine learning.

For example, if the user executes a web browser, the controller 110 may infer a user visual fatigue occurrence time, a visual fatigue duration time, a visual fatigue occurrence cycle, etc. corresponding to the execution of the web browser by using a visual fatigue DB without bio-information of the user (e.g., EEG information) received from the wearable apparatus 200.

If the visual fatigue of the user increases, the controller 110 may provide the user with another content corresponding to a decrease in the visual fatigue as shown in FIGS. 5A and 11B.

The providing of the other content corresponding to the increase in the visual fatigue without receiving the bio-information of the user (e.g., EEG information) from the wearable apparatus 200 is similar to providing of another content corresponding to the decrease in the visual fatigue as shown in FIGS. 5A and 11B, and thus a repeated description thereof is omitted.

According to another embodiment of the present disclosure, the server 300 that receives bio-information of the user (e.g., EEG information) transmitted from the wearable apparatus 200 may calculate a visual fatigue.

The wearable apparatus 200 may transmit detected bio-information of the user (e.g., EEG information) to the server 300. The portable apparatus 100 may transmit application information (e.g., an application type, a content type, an application execution start time, or the like) corresponding to an executed application to the server 300.

A controller (not shown) of the server 300 may calculate the visual fatigue based on the bio-information of the user (e.g., EEG information) received from the wearable apparatus 200 and the application information received from the portable apparatus 100. The controller may store a visual fatigue DB corresponding to the calculated visual fatigue in a storage unit (not shown) of the server 300. Visual fatigue items included in the visual fatigue DB may include an ID for a history management, an application type (e.g., a webpage, a video, a game, or the like) executed in the portable apparatus 100, a content type (e.g., a webpage, a video, a game, or the like), an application execution start time, a visual fatigue occurrence time, a visual fatigue duration time, a visual fatigue occurrence cycle, user fatigue bio-information (e.g., a heart rate, a temperature, of the like if a visual fatigue occurs), another content change information (e.g., another content type, another content change start time, or the like), etc.

The controller of the server 300 may manage a visual fatigue history of the user by using an accumulated visual fatigue DB. The controller of the server 300 may learn the visual fatigue of the user by using the stored visual fatigue DB and machine learning. The controller 110 may learn the visual fatigue of the user by using the stored visual fatigue DB, a statistical analysis, a big data analysis, or machine learning. The statistical analysis may refer to a regression analysis, a time-series analysis, or an analysis using an execution of a regular check or the like in statistical software. A computing apparatus may extract (or search for), analyze, and determine a pattern of accumulated big data, and infer a result through machine learning.

The controller (not shown) of the server 300 may infer a visual fatigue through an accumulation of visual fatigue learning. The controller of the server 300 may inter a visual fatigue of the user by using a stored visual fatigue DB, a statistical analysis, a big data analysis, or machine learning.

The controller of the server 300 may transmit visual fatigue information corresponding to the calculated visual fatigue to the portable apparatus 100 through a communicator (not shown). For example, the visual fatigue information may include an application type, a content type, a current visual fatigue index, a visual fatigue occurrence time, a visual fatigue duration time, etc.

If the calculated visual fatigue of the user increases (e.g., if the visual fatigue is higher than or equal to 2.6), the controller of the server 300 may transmit visual fatigue information corresponding to the increased visual fatigue of the user to the portable apparatus 100.

If the visual fatigue information corresponding to the increase in the visual fatigue is received from the server 300, the controller 110 of the portable apparatus 100 may provide the user with one of other contents corresponding to the increase in the visual fatigue as shown in FIGS. 5A and 11B.

The providing of the other contents corresponding to the visual fatigue information received from the server 300 is similar to the providing of other contents corresponding to the increase in the visual fatigue as shown in FIGS. 5A and 11B, and thus a repeated description thereof is omitted.

According to another embodiment of the present disclosure, the server 300 may infer a visual fatigue without bio-information of the user transmitted from the wearable apparatus 200.

The server 300 may not be connected to the wearable apparatus 200, which detects bio-information of the user (e.g., EEG information), through a communicator (not shown) but may receive application information (e.g., an application type, a content type, an application execution start time, or the like) corresponding to an application executed in the portable apparatus 100.

The controller may store a visual fatigue DB corresponding to a pre-calculated visual fatigue in a storage unit (not shown) of the server 300. Visual fatigue items included in the visual fatigue DB may include an ID for a history management, an application type (e.g., a web browser, a video player, a game, or the like) executed in the portable apparatus 100, a content type (e.g., a webpage, a video, a game, or the like), an application execution start time, a visual fatigue occurrence time, a visual fatigue duration time, a visual fatigue occurrence cycle, user fatigue bio-information (e.g., a heart rate, a temperature, or the like if a visual fatigue occurs), etc.

The controller of the server 300 may manage a visual fatigue history of the user by using an accumulated visual fatigue DB. The controller of the server 300 may learn a visual fatigue of the user by using a stored visual fatigue DB and machine learning without bio-information of the user (e.g., EEG information) received from the wearable apparatus 200. The controller may learn the visual fatigue of the user by using a stored visual fatigue DB, a statistical analysis, a bid data analysis, or machine learning. The statistical analysis may refer to a regression analysis, a time-series analysis, or an analysis using an execution of a regular check or the like in statistical software. A computing apparatus may extract (or search for), analyze, and determine a pattern of bid data, and inter a result through machine learning.

The controller of the server 300 may infer the visual fatigue through an accumulation of visual fatigue learning. The controller of the server 300 may infer a visual fatigue of the user by using a stored visual fatigue DB, a statistical analysis, a big data analysis, or machine learning.

The controller of the server 300 may transmit visual fatigue information corresponding to the inferred visual fatigue to the portable apparatus 100 through a communicator (not shown). For example, the visual fatigue information may include an application type, a content type, a current visual fatigue index, a visual fatigue occurrence time, a visual fatigue duration time, etc.

If the calculated visual fatigue of the user increases (e.g., if the visual fatigue is higher than or equal to 2.6), the controller of the server 300 may transmit the visual fatigue information corresponding to the increased visual fatigue of the user to the portable apparatus 100 through the communicator (not shown).

If the visual fatigue information corresponding to the increase in the visual fatigue is received from the server 300, the controller 110 of the portable apparatus 100 may provide the user with one of other contents corresponding to the increase in the visual fatigue as shown in FIGS. 5A and 11B.

The providing of the other contents corresponding to the visual fatigue information received from the server 300 is similar to the providing of the other contents corresponding to the increase in the visual fatigue as shown in FIGS. 5A and 11B, and thus a repeated description thereof is omitted.

Methods according to various embodiments of the present disclosure may be embodied as a program code form that may be performed through various types of computer units and then may be recorded on a computer readable recording medium. The computer readable recording medium may include a program command, a data file, a data structure, or a combination thereof. Examples of the computer readable recording medium may include a volatile or nonvolatile storage device such as an ROM or the like regardless of being detectable or being rewritable, a memory such as an RAM, a memory chip, a device, or an integrated circuit (IC), and a storage medium on which recording may be optically or magnetically performed and which may be read in a machine language (e.g., a computer) such as a CD, a DVD, a magnetic disk, a magnetic tape, or the like.

A memory that may be included in a portable apparatus may be an example of a storage medium that may store a program including instructions embodying various embodiments of the present disclosure and may read in a machine language. Program commands recorded on the computer readable recording medium may be particularly designed and configured for the present disclosure or may be well known to and used by computer software developers.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. A method of changing a content screen of a portable apparatus, the method comprising:
    displaying content;
    determining whether a value of a visual fatigue is higher than a threshold value using a model trained by machine learning;
    based on the determining that the value of the visual fatigue is higher than the threshold value, displaying a user interface (UI) indicating an increase of the visual fatigue and a guide for changing a layout of the content on the content; and
    based on a user request being input while the UI is displayed, changing the layout of the content.

2. The method of claim 1, wherein the changing of the layout of the content comprises changing at least one of a text, an image, or a moving image that is added to the content.

3. The method of claim 1, wherein the changing of the layout of the content comprises at least one of a change in a font size of the content or an addition of a color screen overlapping the content.

4. The method of claim 1, wherein the method further comprises detecting, by a camera, whether an ocular movement of a user corresponds to an ocular movement guide.

5. The method of claim 1,
    wherein the determining of the value of the visual fatigue is performed by a first application,
    wherein the content is displayed by a second application, and
    wherein the changed layout of the content is differently displayed in response to the second application displaying the content.

6. The method of claim 1,
    wherein the determining comprises determining whether the value of the visual fatigue is higher than the threshold value by inputting bio-information of a user to the model trained by machine learning, and
    wherein the bio-information of the user comprises at least one of electroencephalogram (EEG) information, raw data detected from a wearable apparatus, or digital data generated by processing the raw data.

7. The method of claim 1, wherein the UI is a pop-up window.

8. The method of claim 1, further comprising:
    providing a user feedback corresponding to the increase in the visual fatigue,
    wherein the user feedback comprises at least one of a visual feedback, an auditory feedback, or a haptic feedback.

9. The method of claim 1, further comprising:
    selecting a visual fatigue settings menu; and
    selecting, from the visual fatigue settings menu, at least one of an application setting or a time zone setting,
    wherein the changed layout of the content is displayed according to the selection of the application setting or the time zone setting.

10. The method of claim 1, wherein the method further comprises acquiring bio-information of a user while the content is displayed.

11. A portable apparatus comprising:
    a display configured to display content; and
    at least one processor configured to:
        control the display to display content,
        determine whether a value of a visual fatigue is higher than a threshold value using a model trained by machine learning,
        based on determining that the value of the visual fatigue is higher than the threshold value, display a user interface (UI) indicating an increase of the visual fatigue and a guide for changing a layout of the content on the content, and
        based on a user request being input while the UI is displayed, change the layout of the content.

12. The portable apparatus of claim 11, wherein the at least one processor is further configured to:
    determine whether the value of the visual fatigue is higher than the threshold value by input of bio-information of a user to the model trained by machine learning.

13. The portable apparatus of claim 11, further comprising:
    a camera,
    wherein the camera is configured to detect whether an ocular movement of a user corresponds to an ocular movement guide.

14. The portable apparatus of claim 11, wherein the at least one processor is further configured to display a color screen in response to an application displaying the content.

15. The portable apparatus of claim 11, further comprising:
- a camera,
    - wherein the at least one processor is further configured to perform at least one of eye-tracking or iris recognition using the camera.

16. The portable apparatus of claim 11, wherein, in response to a decrease of the visual fatigue based on the changed layout of the content, the at least one processor is further configured to restore the changed layout of the content to an original layout of the content.

17. The portable apparatus of claim 11,
- wherein the display is further configured to display a visual fatigue settings menu,
- wherein the at least one processor is further configured to receive a selection, from the visual fatigue settings menu, of at least one of an application setting or a time zone setting, and
- wherein the changed layout of the content is displayed according to the selection of the application setting or the time zone setting.

18. The portable apparatus of claim 11, wherein the at least one processor is further configured to:
- request a detection of bio-information of a user from a wearable apparatus through a communicator, and
- acquire bio-information of the user from the wearable apparatus while the content is displayed.

* * * * *